US011363419B2

(12) United States Patent
Ayers et al.

(10) Patent No.: US 11,363,419 B2
(45) Date of Patent: Jun. 14, 2022

(54) INTELLIGENT LOCATION ESTIMATION FOR ASSETS IN CLINICAL ENVIRONMENTS

(71) Applicant: Hill-Rom Services, Inc., Batesville, IN (US)

(72) Inventors: Brandon M. Ayers, Carrboro, NC (US); Frederick C. Davidson, Apex, NC (US); Stephen R. Embree, Chapel Hill, NC (US); Matthew D. Morgan, Cary, NC (US); Kenzi L. Mudge, Raleigh, NC (US); Britten J. Pipher, Fuquay-Varina, NC (US); Eugene G. Urrutia, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/111,075

(22) Filed: Dec. 3, 2020

(65) Prior Publication Data

US 2021/0176600 A1    Jun. 10, 2021

Related U.S. Application Data

(60) Provisional application No. 62/946,165, filed on Dec. 10, 2019.

(51) Int. Cl.
*H04W 4/029* (2018.01)
*G16H 40/67* (2018.01)
(Continued)

(52) U.S. Cl.
CPC ............ *H04W 4/029* (2018.02); *G01S 5/016* (2020.05); *G01S 5/0226* (2013.01);
(Continued)

(58) Field of Classification Search
CPC ............ H04W 4/029; G01S 5/04; G01S 5/06
See application file for complete search history.

(56) References Cited

U.S. PATENT DOCUMENTS 6,456,239 B1 * 9/2002 Werb .................. G01S 5/02
705/28
7,817,046 B2   10/2010 Coveley et al.
(Continued)

FOREIGN PATENT DOCUMENTS

EP   2772772 A1   9/2014
WO   2005062066 A2   7/2005

OTHER PUBLICATIONS

European Search Report, Application No. EP 20 21 2505, dated Apr. 26, 2021, 8 pages.

*Primary Examiner* — Qutbuddin Ghulamali
(74) *Attorney, Agent, or Firm* — Merchant & Gould P.C.

(57) ABSTRACT

A system identifies a first position of a tag in a clinical environment based on first times at which first receivers received a first wireless signal from the tag. The system estimates a second position of the tag in the clinical environment based on second times at which second receivers received a second wireless signal from the tag. The system determines that a boundary is located between the first position and the second position, defines a path range around the first position of the tag based on an expected movement of the tag during a time interval between the first and second wireless signals, determines that the boundary lacks a door within the path range, adjusts the second position of the tag based on the boundary map, and transmits a message indicating that the tag is located at the adjusted position at the second time.

17 Claims, 17 Drawing Sheets

(51) Int. Cl.
*G16H 40/20* (2018.01)
*H04W 4/33* (2018.01)
*G01S 5/02* (2010.01)
*G01S 5/00* (2006.01)
*G07C 9/00* (2020.01)
*H04W 4/02* (2018.01)
G01S 5/04 (2006.01)
G01S 5/06 (2006.01)

(52) U.S. Cl.
CPC .............. *G01S 5/0244* (2020.05); *G07C 9/00* (2013.01); *G16H 40/20* (2018.01); *G16H 40/67* (2018.01); *H04W 4/023* (2013.01); *H04W 4/33* (2018.02); *G01S 5/04* (2013.01); *G01S 5/06* (2013.01)

(56) References Cited

U.S. PATENT DOCUMENTS

| | | | |
|---|---|---|---|
| 2009/0231136 A1 | 9/2009 | Sugla et al. | |
| 2010/0090901 A1* | 4/2010 | Smith | H04W 4/029 342/451 |
| 2012/0313759 A1* | 12/2012 | Markwitz | G08B 21/22 340/10.1 |
| 2015/0123788 A1* | 5/2015 | Greenberg | H04W 4/02 340/539.13 |
| 2015/0248797 A1 | 9/2015 | Duggan et al. | |
| 2015/0355311 A1 | 12/2015 | O'Hagan et al. | |
| 2019/0124475 A1 | 4/2019 | Swart | |

* cited by examiner

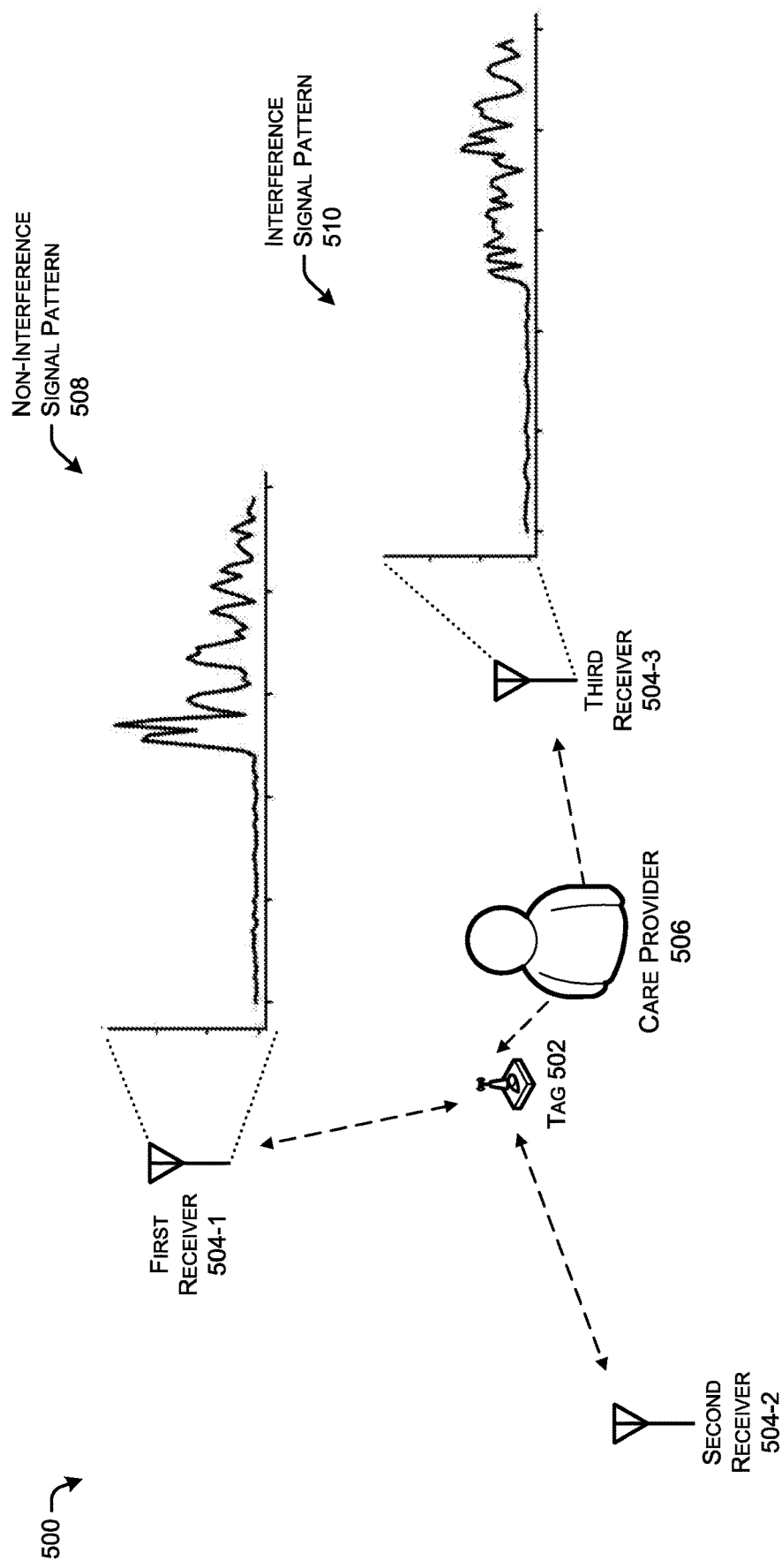

INTELLIGENT LOCATION ESTIMATION FOR ASSETS IN CLINICAL ENVIRONMENTS

TECHNICAL FIELD

This application relates generally to a Real Time Locating System (RTLS) configured to track the locations of assets in a clinical environment by using barrier maps to improve the accuracy of tracking and/or correcting for the influence of users on wireless signals transmitted between tags and receivers.

BACKGROUND

Hospitals, and other types of healthcare environments, track a variety of different assets, and determining/monitoring the locations of such assets can be important when administering care to patients. For instance, the positions of medical devices, hospital beds, and other clinically-relevant objects may be relevant to providing and maintaining a high level of care in these environments. In various examples, the positions of patients may be significant for managing their care. In various cases, the positions of care providers (e.g., nurses, physicians, and the like) may also be important for efficiently delivering care in the clinical environment. Tracking the positions of these and other clinically-relevant assets in real time can enable centralized systems (e.g., nurse call systems) within the clinical environment to efficiently deploy resources to care for the patients in the clinical environment.

A Real-Time Location System (RTLS) can be used to track the locations of objects and people in various settings. In the RTLS, a tag may emit a wireless signal that can be received by multiple receivers. Based on the times-of-flights (or angles-of-arrival) of the wireless signal being received by the multiple receivers, and the positions of the receivers, a tag's location can be derived within an environment.

However, broad adoption of RTLS in healthcare settings to track objects, patients, and care providers is not without challenges. There is a need for more accurate RTLS technologies adapted for various healthcare environments. In addition, due to significant variances between various healthcare environments, there is a need for a flexible RTLS platform that can be adapted for various clinical settings.

SUMMARY

Various implementations of the present disclosure relate to a location system with improved location-tracking capabilities. The system may be an RTLS. Some example implementations disclosed herein can be adapted for a healthcare environment and can be used to track the locations of assets in the environment. For instance, a system can accurately track objects (e.g., medical devices), patients, and care providers within a clinical environment.

In some instances, a location system can utilize contextual information about the physical layout of an environment to enhance its accuracy. The RTLS system may use a "boundary" (or "wall") map of the environment to determine whether measurements of a tag appear suspiciously inaccurate. For instance, if a tag appears to pass through a wall without a doorway or other threshold nearby, the RTLS system may presume that the estimated location of the tag is inaccurate, and may take actions to correct the estimated location of the tag. In some cases, the RTLS system may correct the estimated location of the tag based on the boundary map. For instance, the system may adjust the estimated location of the tag to be on the same side of the wall as its last known location.

In some implementations, a location system tracking a tag worn by, carried by, or otherwise attached to a person can correct for the influence of the person on the propagation of a signal emitted by the tag. In various cases, the signal may be attenuated, slowed down, and/or refracted as it encounters the person's body. The system may identify whether the person is located between a particular receiver and the tag as the tag is transmitting the wireless signal to the receiver. The system may estimate the influence of the person's body on how the wireless signal is received by the receiver. When the measurements (e.g., the time at which it receives) the wireless signal, the system may automatically adjust those measurements based on the influence of the person's body.

Various implementations disclosed herein provide technical improvements to the fields of RTLS-based tracking. In particular, various implementations can be used to more accurately track assets in a clinical environment, such as a hospital.

DESCRIPTION OF THE FIGURES

The following figures, which form a part of this disclosure, are illustrative of described technology and are not meant to limit the scope of the claims in any manner.

FIG. 5 illustrates an example location system environment for correcting the estimated position of a tag based on the position of a person associated with the tag.

DETAILED DESCRIPTION

Figure 1:
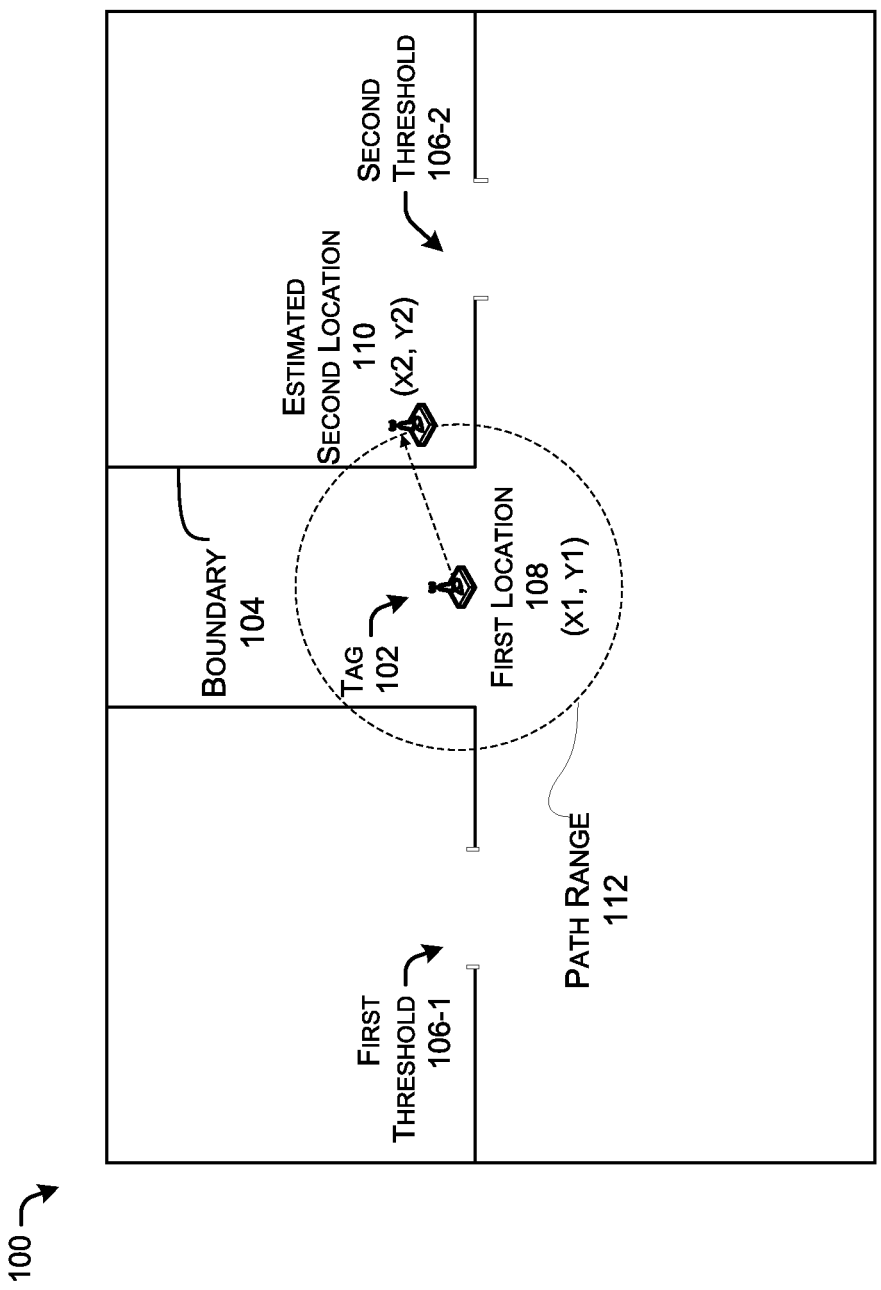
FIG. 1 illustrates an example clinical environment for tracking the location of an asset in a clinical environment.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example clinical environment 100 for tracking the location of an asset in a clinical environment. The asset may be associated with a tag 102. As used herein, the term "tag" can refer to a physical device capable of storing information, transmitting information to a remote device, and/or receiving information from a remote device. A tag may be attached to a physical object (e.g., a medical device, a hospital bed, or the like). In various implementations, a tag can be passive, such that it collects energy from outside sources (e.g., radio waves) to power storage, data transmission, processing, or the like. In some implementations, a tag can be active, such that it may include a power source that can be used to power storage, data transmission, processing, or the like. Some examples of tags include Radio-Frequency Identification (RFID) tags, which can use electromagnetic signals to communicate with external devices. However, some tags can use non-radio-frequency electromagnetic signals, acoustic signals, or the like to communicate with external devices.

In some cases in which the asset is an object (e.g., a medical device, a hospital bed, or the like), the tag 102 may be attached to the object. In some instances in which the asset is a person (e.g., a patient, care provider, or the like), the tag 102 may be worn by the person. In some instances, the tag may be worn on a lanyard or necklace around the person's neck. In some examples, the tag may be integrated into a wristband that is worn by the person. In some instances, the tag may be integrated into clothes worn by the person.

According to some example implementations, the clinical environment 100 may be a floor of a building. In some cases, the clinical environment 100 may have at least one boundary 104, which may be a wall or the like. Further, the boundary 104 may be a fence, a window, or some other solid boundary that solid objects cannot easily pass through. Although FIG. 1 illustrates a single, continuous boundary 104, various implementations can include multiple boundaries. In addition, throughout the clinical environment 100, the boundary 104 may be interrupted by thresholds, such as a first threshold 106-1 and second threshold 106-2. As used herein, the term "threshold" may refer to a door, a gate, an opening, a window, or any other break in the boundary 104 that can be traversed by solid objects.

In various implementations, the boundary 104 and the thresholds 106-1 and 106-2 can be identified using a boundary map. The boundary map may represent the locations of various boundaries and thresholds within the environment 100. In some cases in which the environment 100 is represented in two dimensions, the boundary map can represent the locations of the boundary 104 and the thresholds 106-1 and 106-2 within an x-y coordinate system. A location system, such an RTLS, can utilize the boundary map to accurately predict the location of the tag 102 and the asset. Various examples of a location system are described below with reference to FIGS. 7 to 11. In some implementations, the location system can include a system or a device that includes at least one processor executing various instructions stored in memory. Accordingly, actions performed by the location system can be performed by the processor(s) in the location system.

In various implementations, the tag 102 may be identified at a first location 108 within the environment 100 by the location system. The first location 108 may be represented in the x-y coordinate system by the coordinates $(x_1, y_1)$. In addition, the tag 102 may be estimated to be at a second location 110 within the environment 100 by the location system. The second location may be represented in the x-y coordinate system by the coordinates $(x_2, y_2)$. The location system may determine first location 108 by a first wireless signal transmitted by the tag 102, and estimate the estimated second location 110 based on a second wireless signal transmitted by the tag 102. The first wireless signal may be generated and/or sent before the second wireless signal. In some cases, the first and second wireless signals are consecutive signals transmitted by the tag 102. Accordingly, the estimated second location 110 may be estimated to be a subsequent position of the tag 102 after the tag 102 is located at the first location 108.

In example implementations, the system may identify and/or estimate the locations of the tag 102 by performing trilateration, multilateration, triangulation, or the like. For example, the location system can determine time lags of the wireless signals transmitted between the tag 102 and various receivers associated with the location systems based on the transmission times and the reception times (or based on a one-way transmission time derived from a Round Trip Time (RTT)), and can determine the distances between the tag 102 and the receivers by multiplying the time lags by the velocity of the wireless signals. In some cases, the locations of the tag 102 can be derived based on discrepancies between reception times of the same wireless signal by different receivers in the environment 100. Some example instances are described in more detail below with reference to FIG. 7.

Using the boundary map, the location system may identify that the boundary 104 is located between the first location 108 and the estimated second location 110. For instance, the RTLS may determine that a line segment defined between the first location 108 and the estimated second location 110 intersects the boundary 104 by comparing the line to the boundary map. Because the tag 102 cannot cross the boundary 104 without a break within the boundary 104, the location system may perform additional actions to confirm whether the estimated second location 110 is accurate.

The location system may confirm whether the tag 102 may have traversed a threshold (e.g., the first threshold 106-1 or the second threshold 106-2) in the boundary 104 in order to cross the boundary 104 and arrive at the estimated second location 110. In some implementations, the location system may determine an expected range of movement of the tag 102 in a time interval between the first wireless signal and the second wireless signal. For instance, if the tag 102 is associated with a care provider, the expected range of movement of the tag 102 may be a walking speed of the care provider multiplied by the time interval. In some cases, the walking speed can be estimated based on a predetermined walking speed, such as 5 miles per hour. In various examples, the walking speed can be estimated based on previously tracked movements of the care provider. For instance, if the care provider has previously moved at a pace of 7 miles per hour, the walking speed may be 7 miles per hour. In some instances, the walking speed may be an average speed of the care provider, a maximum speed of the care provider, or a combination thereof. The location system may also estimate an expected range of error associated with its own capabilities of estimating the location of the tag 102. For instance, the expected range of error can be determined based on historical trends, the density of receivers picking up the first and second signals within the environment 100, a sensitivity of the receivers picking up the first and second signals, or the like. According to some examples, the expected range of error is calculated by preliminarily testing the location system's accuracy. For instance, the tag 102 may be placed in a known location, the location system may estimate the position of the tag 102 to generate an estimated location, and the known location and the estimated location can be compared. In some cases, the expected range of error can be added to the expected range of movement of the tag 102. Based on the expected range of movement of the tag 102, the location system may determine a path range 112 representing an expected range of paths that the tag 102 could move in the time interval between transmitting the first signal and the second signal. The path range 112 may be represented by a circle, an ellipse, a square, and/or any other shape that is centered at the first location 108. In some cases, a radius of the path range 112 can be the sum of the expected range of movement and the expected range of error of the location system.

In various implementations, the location system may determine whether a threshold in the boundary 104 exists at least partly within the path range 112. If a threshold, such as the first threshold 106-1 or the second threshold 106-2, is located at least partly within the path range 112, then the RTLS may determine that there is a possible path by which the tag 102 traversed the boundary 104. Such a path may extend, for example, from a previous location of the tag 102 to an additional location of the tag 102 (e.g., to the estimated second location 110), and such a path may pass through the threshold disposed at least partly within the path range 112. When a threshold is determined to be within the path range 112, the location system may confirm that the second location 110 is accurate and report the estimated second location 110 as the location of the tag 102.

However, as shown in FIG. 1, the boundary 104 may lack a threshold within the path range 112. That is, the second threshold 106-2 in the boundary 104 is not even partly located within the path range 112. When the location system determines that the boundary 104 lacks a threshold within the path range 112, the location system may identify that the estimated second location 110 is inaccurate. The location system may correct the estimated second location 110.

Figure 2:
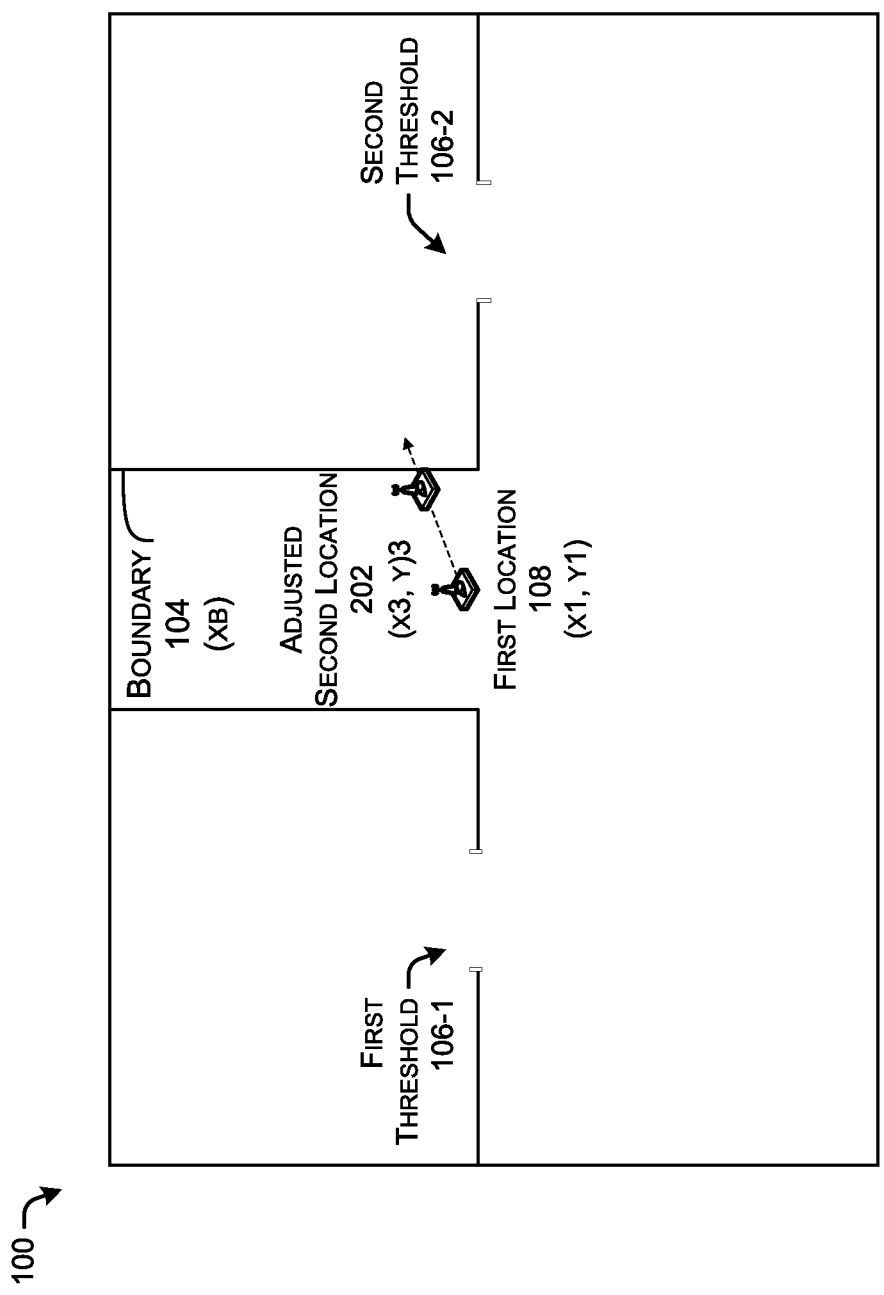
FIG. 2 illustrates an example environment indicating how a subsequent location can be corrected according to various implementations of the present disclosure.

FIG. 2 illustrates an example environment 200 indicating how the second location 110 can be corrected according to various implementations of the present disclosure. In various implementations, upon identifying that the boundary 104 lacks a threshold within the path range 112, the location system may identify an adjusted second location 202 of the tag 102 based on the boundary map. The adjusted second location 202 may also be referred to as a "corrected second location 202." The adjusted second location 202 may be on the same side of the boundary 104 as the first location 108. That is, the boundary 104 may not be disposed between the first location 108 and the adjusted second location 202. The adjusted second location 202 may be represented in the x-y coordinate system by the coordinates $(x_3, y_3)$.

In various implementations, the adjusted second location 202 may lie on the line segment defined between the first location 108 and the estimated second location 110. In some example implementations, the line segment may be defined by the following Formula 1:

$$y_n = \left(\frac{y_2 - y_1}{x_2 - x_1}\right)x_n + \left(\frac{x_1 y_2 - x_2 y_1}{x_2 - x_1}\right)$$

wherein $x_1 \leq x_n \leq x_2$ and $y_1 \leq y_n \leq y_2$, and $(x_n, y_n)$ represents any point on the line segment. Accordingly, the corrected location may be one example of $(x_n, y_n)$ coordinates.

In some examples, the location system may determine the adjusted second location 202 by decreasing the distance between the first location 108 and the estimated second location 110 by consecutive percentages until the first location and the adjusted second location 202 are located on the same side of the boundary 104. For instance, the location system may decrease the distance by a percentage (e.g., 5%, 10%, or the like) and check whether the percentage adjustment would place the adjusted second location 202 on the same side of the boundary 104 as the first location 108. If the percentage adjustment is sufficient, the location system may confirm the adjusted second location 202. If the percentage adjustment is insufficient, the location system may perform an additional adjustment on the adjusted second location 202 (e.g., a decrease in the distance by another 5%, 10%, or the like).

In various implementations, the location system may use the coordinates of the boundary 104 provided in the boundary map to automatically generate the adjusted second location 202. The location system may identify that the boundary 104 is represented by a series of x-y coordinates, or by an equation within the x-y coordinate system. For instance, the boundary 104 depicted in FIG. 1 may be defined according to a dataset of x-y coordinates. The coordinates of the first location 108 $(x_1, y_1)$ may be compared to the dataset of the boundary 104, to determine whether $x_1$ is less than, equal to, or greater than the x coordinates of the dataset representing the boundary 104 and whether $y_1$ is less than, equal to, or greater than the y coordinates of the dataset representing the boundary 104. In the implementation depicted in FIG. 2, the $x_1$ value of the first location 108 may be less than the x coordinates of the dataset. Accordingly, the location system may identify that the $x_3$ value of the adjusted second location 202 should also be less than the x coordinates of the boundary 104.

In some cases, the location system may input the dataset representing the boundary 104 into Formula 1, in order to find the point of intersection between the line segment and the boundary 104. In some cases, the location system may define the adjusted second location 202 to be at the point of intersection, or slightly (e.g., half the thickness of the boundary, such as 4 inches or the like) toward the first location 108 from the boundary 104. In some cases, the boundary map defines both surfaces of the boundary 104. Accordingly, the adjusted second location 202 may be defined according to the inner surface of the boundary 104 facing the first location 108.

In an example, because boundary 104 is defined vertically in the x-y coordinate system, the boundary map may indicate that an inner surface of the boundary 104 is represented by $x_b=a$, wherein $d<y_b<e$, and a, d, and e are each constants. The location system may input the value of $x_b=a$ as the $x_n$ value of Formula 1 to calculate a corresponding $y_n$ value. The coordinates $(x_3, y_3)$ can be defined such that $x_3=x_b$ (or slightly less than $x_b$), and $y_3$=the corresponding $y_n$ value.

Various clinical environments, such as environment 100, have numerous boundaries (e.g., boundary 104) that make it difficult to accurately assessing the location of tags (e.g., the tag 102) based on wireless signals between the tags and the receivers. Boundaries may attenuate, reflect, and/or slow down wireless signals, thereby lowering the accuracy of the location system. According to various implementations described herein, the location system can confirm and/or correct the estimated location of the tag 102 based on a boundary map of the environment 100. The accuracy of the location system can therefore be improved.

Figure 3:
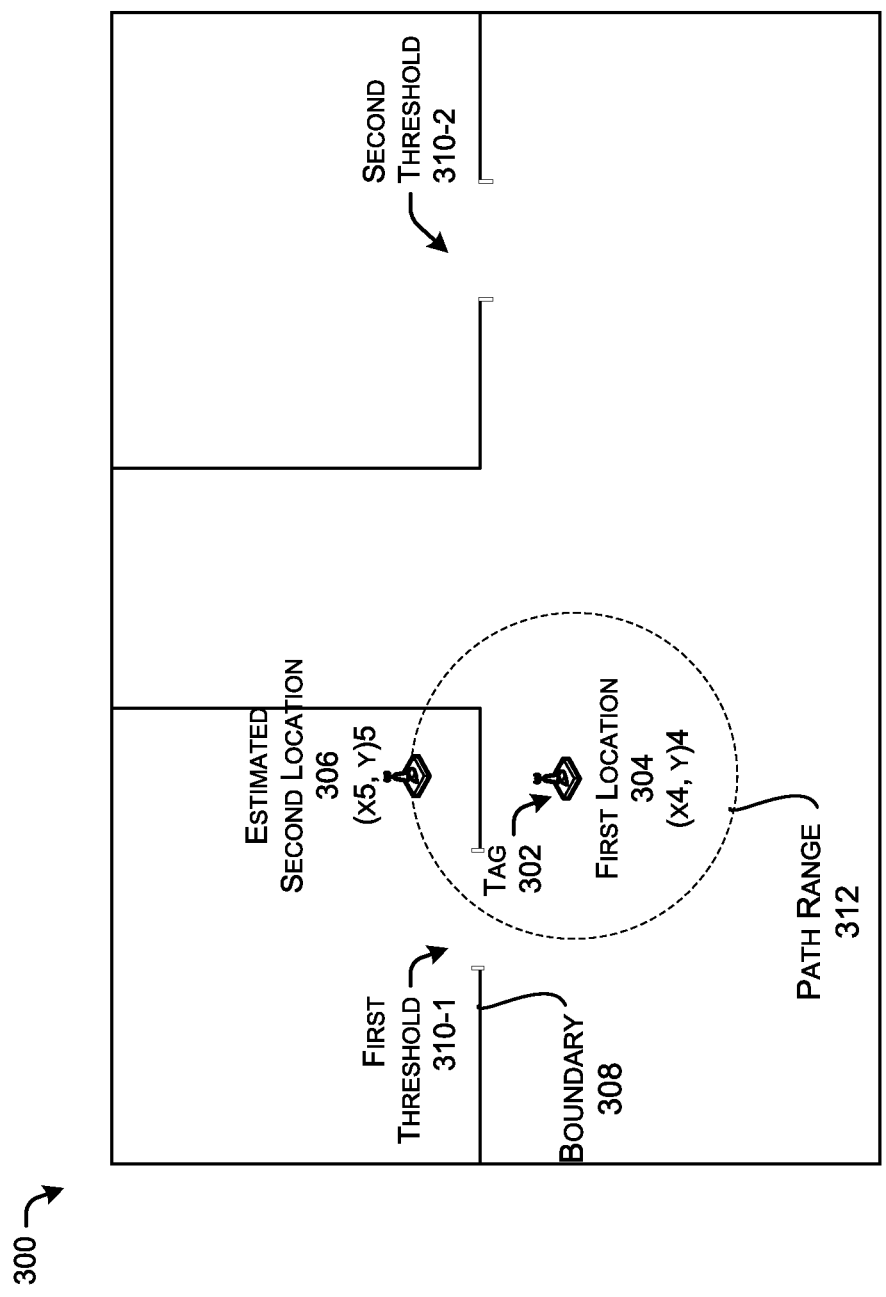
FIG. 3 illustrates an example environment in which a location system confirms a subsequent location of a tag that has moved from one side of a boundary to another.

FIG. 3 illustrates an example environment 300 in which a location system confirms a subsequent location of a tag that has moved from one side of a boundary to another. Similar to FIGS. 1 and 2, the environment 300 includes a tag 302 that is determined to move from a first location 304 (defined by the coordinates $(x_4, y_4)$) to an estimated second location 306 (defined by the coordinates $(x_5, y_5)$). The environment 300 may include a boundary 308 with various thresholds, such as a first threshold 310-1 and a second threshold 310-2. The location system may be an RTLS. In various implementations, the location system may include at least one processor that executes various instructions stored in memory. Accordingly, actions of the location system can be performed by the processor(s).

The location system may identify that the boundary 308 exists between the first location 304 and the estimated second location 306 using a boundary map of the environment 300. The location system may identify a path range 312 around the first location 304. However, unlike the implementations discussed illustrated in FIGS. 1 and 2, the location system may determine that the first threshold 310-1 is at least partially within the path range 312. The location system may make this determination using the boundary map. Upon determining that the first threshold 310-1 is in the path range 312, the location system may confirm the estimated second location 306 as the position of the tag 302.

Figure 4:
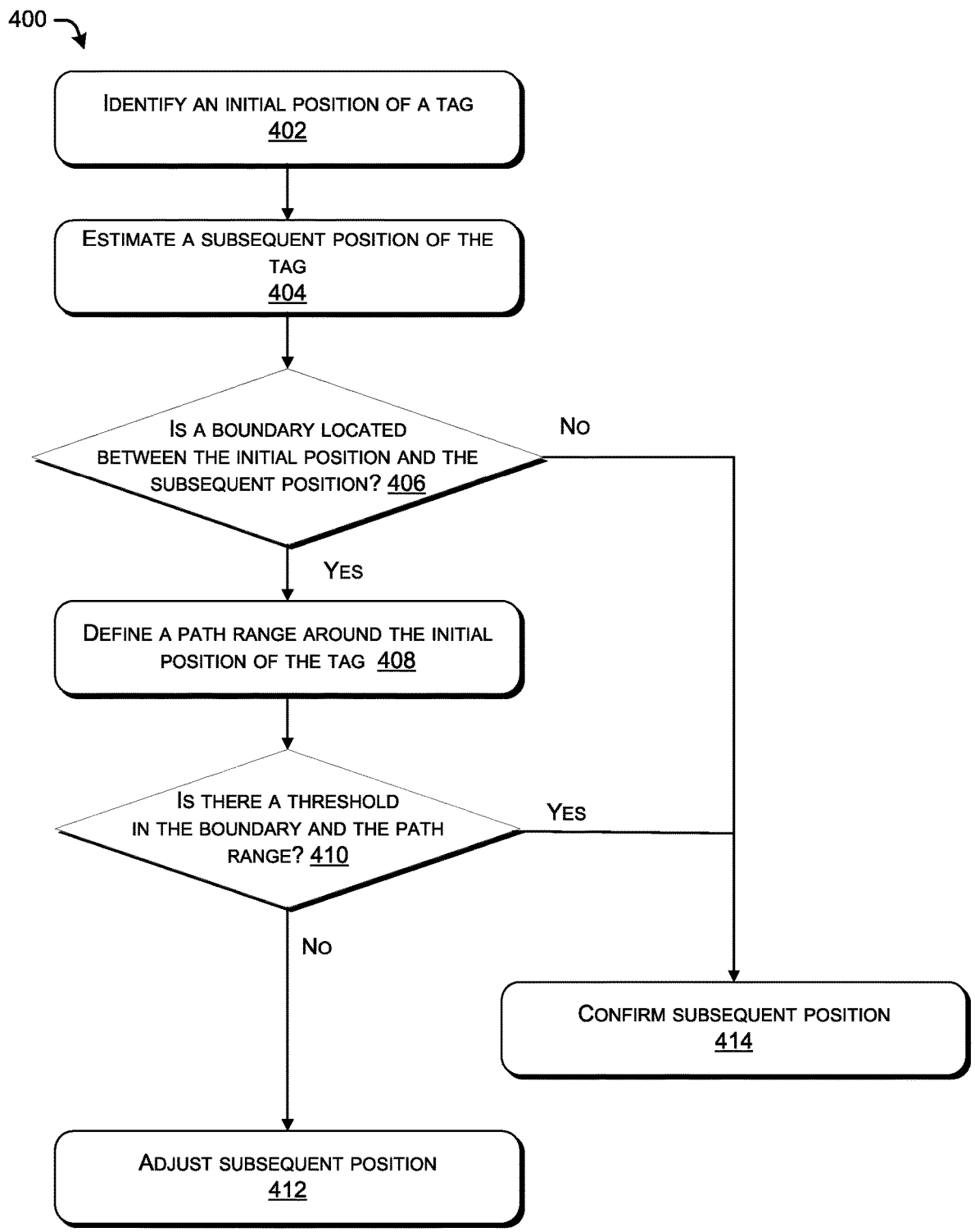
FIG. 4 illustrates an example process that can be performed by a location system.

FIG. 4 illustrates an example process 400 that can be performed by a location system. For instance, the process 400 can be performed by the location system 808 described below with reference to FIGS. 8 to 10, the location engines 1006 or 1108 described below with reference to FIGS. 10 and 11, or any other suitable RTLS.

At 402, the system may identify an initial position of the tag. The system may identify the initial position based on the transmission of a first signal from the tag to multiple receivers in an environment. Based on the times at which the receivers receive the first signal, as well as the positions of the receivers, the system may identify the initial position of the tag.

At 404, the system may estimate a subsequent position of the tag. The system may estimate the subsequent position based on the transmission of a second signal from the tag to multiple receivers in the environment. In some cases, the tag may transmit the second signal after the first signal. Based on the times at which the receivers receive the second signal, as well as the positions of the receivers, the system may estimate the subsequent position of the tag.

At 406, the system may determine whether a boundary is located between the initial position and the subsequent position. In some cases, the system can reference a boundary map associated with the environment in order to identify whether the boundary is present between the initial position and the subsequent position. For instance, the system may compare a line segment between the initial position and the estimated subsequent position to the boundary map in order to determine whether the line segment intersects a boundary in the environment.

If the system determines that the boundary is located between the initial position and the subsequent position at 406, the system may define a path range around the initial position at 408. The path range may have a radius that depends on an expected range of movement of the tag. In some cases, the expected range of movement can be based on a movement speed of a care provider associated with the tag and/or a time interval between the wireless signals used to identify the initial position and estimate the subsequent position. For instance, the radius of the path range can be equal to the sum of the expected range of movement and the expected range of error of the RTLS system. The system may define the path range to be centered around the initial position.

At 410, the system may determine whether there is a threshold in the boundary and the path range. For instance, the system may reference the boundary map in order to identify whether a threshold in the boundary is present within the path range. The system may determine that there is a threshold in the path range if a threshold in the boundary is at least partly within the path range.

If the system determines that the boundary lacks a threshold within the path range at 410, the system may adjust the subsequent position at 412. In some cases, the system may adjust the subsequent position to be at a surface of the boundary facing the initial position. In some cases, the system may adjust the subsequent position to be on the same side of the boundary as the initial position.

If, however, the system determines that a boundary is not located between the initial position and the subsequent position at 406, or the system determines that there is a threshold in the boundary within the path range at 410, the system may confirm the subsequent position at 414. In some cases, the system may transmit a message to a reporting system that indicates the subsequent position as the true position of the tag.

FIG. 5 illustrates an example location system environment 500 for correcting the estimated position of a tag 502 based on the position of a person associated with the tag 502. The location system may be an RTLS, in some cases. In various implementations, the tag 502 can transmit wireless (e.g., radio) signals to various receivers in a clinical environment. For instance, as illustrated in FIG. 5, the tag 502 transmits a wireless signal to a first receiver 504-1, a second receiver 504-2, and a third receiver 504-3 in the environment 500.

In general, a system can presume that the wireless signal is transmitted in a straight line through ambient air. However, as illustrated in FIG. 5, the tag 502 may be associated with a care provider 506 whose body is not made of air. The wireless signal may propagate through the air at a different phase velocity than through the body of the care provider 506. The air may have a different index of refraction than the body of the care provider 506, with respect to the wireless signal. Accordingly, when the wireless signal is intercepted by the body of the care provider 506, the wireless signal may be refracted. Specifically, because the care provider 506 is located between the tag 502 and the third receiver 504-3, the wireless signal may travel a greater distance and at a slower speed to get to the third receiver 504-3, than if the body of the care provider 506 was not between the tag 502 and the third receiver 504-3. That is, the time at which the third receiver 504-3 receives the wireless signal may be delayed.

When the wireless signal is refracted by the body of the care provider 506, the wireless signal may slow down and/or change direction. If the location system calculates the position of the tag 502 based on the time-of-flight of the wireless signal as it is transmitted from the tag to the receivers 504-1 to 504-3, the angle-of-incidence of the wireless signal as it is received by the receivers 504-1 to 504-3, discrepancies between times at which the wireless signal is received by the receivers 504-1 to 504-3, or the like, the location system may inaccurately estimate the location of the tag 502 without accounting for a delay associated with the refraction of the wireless signal.

In various implementations, the location system may predict an amount that the wireless signal is delayed due to the presence of the care provider 506. In some cases, the location system may associate a signal pattern of the wireless signal as it is received by one of the receivers 504-1 to 504-3 with the delay. For instance, the location system may implement a machine learning model that can identify features in the signal pattern indicating whether the wireless signal has passed through the care provider 506 during transmission. The machine learning model can be trained based on testing data including signal patterns with known physical interference levels (e.g., the interception levels of the wireless signals by care providers or other users are known).

The wireless signal, as transmitted by the tag 502, may be an Ultra-Wideband (UWB) signal. In accordance with the IEE 802.15.4 standard, an UWB signal can be transmitted as a burst of pulses positioned within the signal's period. However, the wireless signal may be received differently than it is transmitted. As illustrated in FIG. 5, the first receiver 504-1 may receive the wireless signal with a non-interference signal pattern 508. The non-interference signal pattern 508 may be represented as a digital amplitude of the received wireless signal versus an accumulator sample index. The non-interference signal pattern 508, as well as other wireless signals that are transmitted directly from the tag 502 to one of the receivers 504-1 to 504-3 without passing through the care provider 506, may have relatively tall, sharp peaks at the beginning of its duration. For instance, an arithmetic mean of the first 30% of the indices of the non-interference signal pattern 508 may be over twice the level of the arithmetic mean of the last 70% of the indices of the non-interference signal pattern 508.

In contrast, the third receiver 504-3 may receive the same wireless signal with an interference signal pattern 510. The interference signal pattern 510 may be represented as digital amplitude of the received wireless signal versus an accumulator sample index. The interference signal pattern 510 may indicate that the wireless signal has passed through the body of the care provider 506. For instance, unlike the non-interference signal pattern 508, the interference signal pattern 510 may lack the sharp peak(s) at the beginning of the of its duration. In some examples, an arithmetic mean of the first 30% of the indices of the interference signal pattern 510 may be less than twice the level of the arithmetic mean of the last 70% of the indices of the interference signal pattern 510. Due to the differences in the shape between the non-interference signal pattern 508 and the interference signal pattern 510, the location system (e.g., utilizing the machine learning model) may be able to identify that the care provider 506 was not present between the tag 502 and the first receiver 504-1 when the wireless signal was transmitted between the tag 502 and the first receiver 504-1 and/or that the care provider 506 was present between the tag 502 and the third receiver 504-3 when the wireless signal was transmitted between the tag 502 and the third receiver 504-3.

In addition, the location system may predict a delay in the reception time of the wireless signal by the third receiver 504-3 due to the wireless signal's traversal of the care provider 506. For instance, the location system may input the shape of the wireless signal into the machine learning model and the machine learning may output the predicted delay. In various examples, the machine learning model may predict the delay without utilizing a shape and/or size of the body of the care provider 506 as an input.

In some implementations, the location system may associate the interference signal pattern 510 of the third receiver 504-3, with a positional relationship between the tag 502 and the care provider 506. For instance, the location system may input the signal pattern into a first model, which may output the positional relationship between the tag 502 and the care provider 506. As used herein, the term "positional relationship" can refer to the relative positions of two references. For instance, the positional relationship between the tag 502 and the care provider 506 can be the relative positions of the tag 502 and the care provider 506. In some examples, the location system may predict the delay in the reception of the wireless signal based on the positional relationship. For example, the location system may input the positional relationship into a second model, which may output the predicted delay. In some cases, the second model may also utilize a shape and/or size of the body of the care provider 506 as an input. The shape and/or size of the body of the care provider 506 could be estimated as, for example, a cylinder with a predetermined width (e.g., one foot) and a predetermined height (e.g., six feet). In some cases in which the location system identifies the location of the tag 502 in an x-y (i.e., two-dimensional) coordinate system, the expected volume could be represented by a circular area with a predetermined diameter (e.g., one foot). According to some examples, the expected volume could be based on predetermined measurements of the width and/or height of the care provider 506. The expected volume could therefore be customized to the care provider 506. In some cases, machine learning can be used to identify the shape and/or size of the body of the care provider 506 based on the wireless signal as it is received by any of the receivers 504-1 to 504-3.

In some instances, the location system can predict a direction in which the care provider 506 is facing and predict the delay based on the direction. For instance, the location system may identify that the care provider 506 is moving in a particular direction, and may predict that the care provider 506 is also facing in the particular direction. The location system may, for instance, input the predicted angle into a model, which may output the predicted delay. In some cases, the model may also accept, as an input, a location of the receiver (e.g., the first receiver 504-1) that has received the delayed wireless signal. In some cases, the model may also utilize a shape and/or size of the body of the care provider 506 as an input.

In some cases, the location system can predict the direction in which the care provider 506 is facing as well as the relative position between the tag 502 and the care provider 506. In some examples, if the tag 502 is designed to be worn on a lanyard around the care provider's 506 neck, the location system may assume that the tag 502 is positionally located at the front of the care provider's 506 body. Thus, the relative location of the tag 502 with respect to the care provider 506 can be a distance from the care provider 506 in the direction in which the care provider 506 is facing. In some cases, the tag 502 can be predetermined to be 1 inch, 6 inches, or the like from the care provider 506. Based on the direction in which the care provider 506 is facing, the relative position between the tag 502 and the care provider 506, a predicted size and/or shape of the care provider 506, a predicted size and/or shape of the tag 502 itself, and a predicted distance between the tag 502 and the care provider 506, the location system can predict the delay in the reception time of the third receiver 504-3.

In some cases, the location system may identify the probabilities that the care provider 506 is located between the receivers 504-1 to 504-3 based on the positional relationship of the tag 502 and the care provider 506, as well as the direction in which the care provider 506 is facing. For example, the location system may identify an expected volume representing the care provider 506 and identify whether a line projected between an expected position of the tag 502 (e.g., a previous position of the tag 502 or an estimated position of the tag 502 based on the measurements of the receivers 504-1 to 504-3 without adjustment) and a particular receiver intersects the volume. If the location system determines that the line passes through a center portion of the volume, the location system may determine that there is a high likelihood that the care provider 506 is located between the tag 502 and the receiver. If the location system determines that the line passes through a peripheral portion of the volume, the location system may determine that there is a lower likelihood that the care provider 506 is located between the tag 502 and the receiver. If the location system determines that the line does not pass through any portion of the volume, the location system may determine that there is a negligible likelihood that the care provider is located between the tag 502 and the receiver. In some cases, the location system determines the likelihood to be proportional to the amount of the width of the volume that the line intersects. For example, the line passes through the volume by a distance that is equal to the diameter of the volume, the likelihood may be 100%, whereas if the line passes through the volume by a distance that is equal to half of the diameter of the volume, the likelihood may be 50%.

In some cases, the location system may use other strategies for determining the likelihood that the care provider is located between the tag 502 and a given receiver. For example, the location system may identify that a signal strength at the given receiver is lower than an expected value given the timing information. The signal strength may indicate that the wireless signal was attenuated by the body of the care provider 506. Accordingly, the location system may identify that there is a likelihood that the care provider is located between the tag 502 and the receiver based on the signal strength. The location system may predict a delay in the reception time at which a particular receiver receives the wireless signal based on the likelihood.

Based on at least one delay predicted by any of the methods described above, the location system may correct the reception time of the first receiver 504-1 and may identify the location of the tag 502 based on the corrected reception time. For instance, the location system may predict a delay in the reception time at which the particular receiver receives the wireless signal, may adjust the reception time based on the predicted delay, and determine the location of the tag 502 based on the adjusted reception time. In some instances, if the particular receiver measures the time at which the wireless signal is received, the location system may adjust the time to be earlier than the actual time that the signal was received. For example, the location system may assume that the wireless signal is delayed by a particular amount of time (e.g., the predicted delay) due to the body of the care provider 506 and subtract that amount of time from the actual time that the signal was received. In some cases, if the particular receiver measures the angle at which the wireless signal is received, the location system may adjust the angle to be different based on the physics of refraction.

For example, in the example environment 500 depicted in FIG. 5, the location system may determine that there is a high likelihood (e.g., greater than 50% likelihood) that the care provider 506 is located between the tag 502 and the third receiver 504-3 based on the interference signal pattern 510. If the third receiver 504-3 receives a wireless signal emitted by the tag 502 at a particular time $t_1$, the location system may subtract a predetermined delay associated with the body of the care provider 506 from the particular time $t_1$ to generate an adjusted time $t_2$. In some cases, the location system may determine an appropriate delay based on the likelihood (e.g., the delay is proportional to the likelihood), and subtract the appropriate delay from the particular time $t_1$ to generate the adjusted time $t_2$. The location system may estimate the position of the tag 502 as though the third receiver 504-3 received the signal at $t_2$, rather than $t_1$. Furthermore, the location system may determine that there is a relatively low likelihood that the care provider 506 is located between the tag 502 and the first receiver 504-1, as well as a relatively low likelihood that the care provider 506 is located between the tag 502 and the second receiver 504-2. Accordingly, the location system may refrain from adjusting the measurements of the wireless signal by the first and second receivers 504-1 and 504-2 before estimating the position of the tag 502.

Figure 6A:
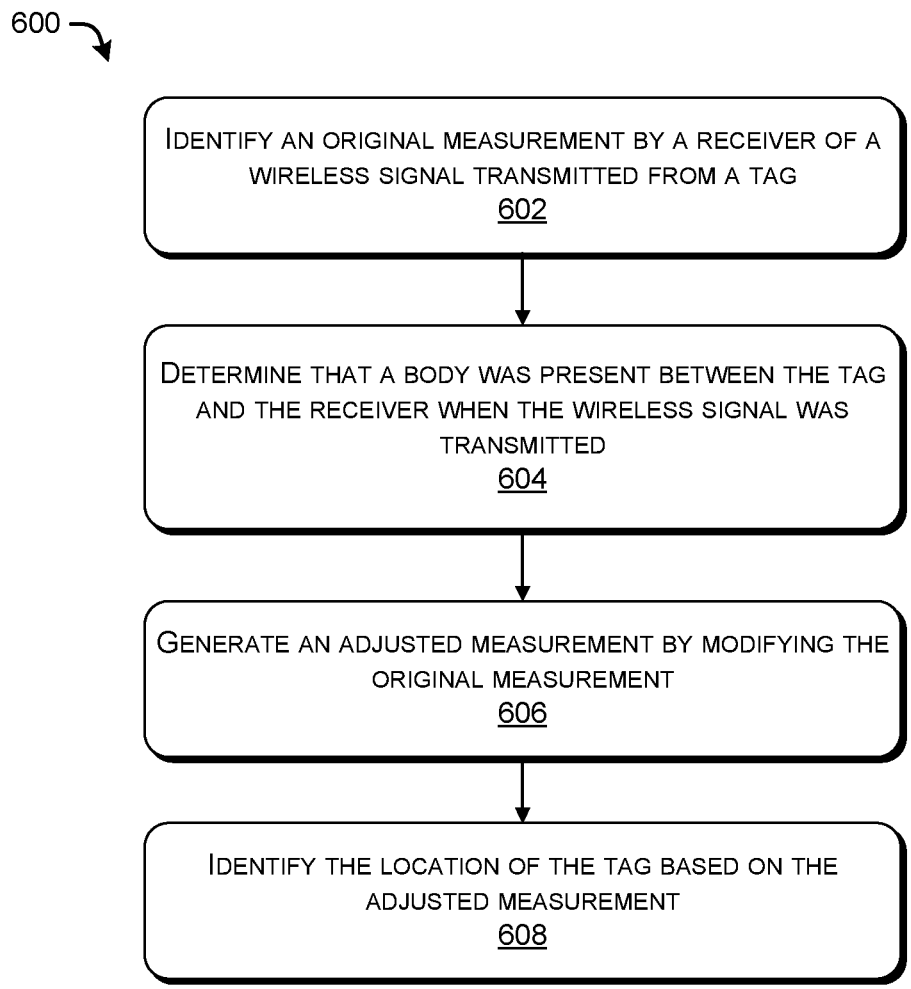
FIGS. 6A and 6B illustrate example processes for taking into account the position of a user in identifying the location of a tag in an environment.

FIG. 6A illustrates an example process 600 for taking into account the position of a user in identifying the location of a tag in an environment. In some examples, the process 600 can be performed by a location system, such as the location system 808 described below with reference to FIGS. 8 to 10, the location engines 1006 or 1108 described below with reference to FIGS. 10 and 11, or any suitable RTLS.

At 602, the system may identify an original measurement by a receiver of a wireless signal transmitted from a tag. The original measurement may be a reception time of the wireless signal by the receiver. In some cases, the wireless signal may be received over a time interval, and the receiver may generate a waveform representing a power, intensity, or amplitude of the received wireless signal over time. In some cases, the original measurement may further include a reception time of the wireless signal by the receiver. In some cases, the reception time corresponds to a time associated with a beginning of the time interval, a peak amplitude of the received wireless signal during the time interval, or an end of the time interval.

At 604, the system may determine that a body was present between the tag and the receiver when the wireless signal was transmitted. The body may be a care provider, in some cases. In various examples, the system may assess the shape of the waveform to determine that the shape of the waveform is consistent with an interference signal pattern. For instance, the beginning of the waveform may lack large sharp peaks indicative of a non-interference signal pattern. In some cases, the system may utilize a trained machine learning model to determine that the shape of the waveform indicates that the body was present between the tag and the receiver when the wireless signal was transmitted between the tag and the receiver.

At 606, the system may generate an adjusted measurement by modifying the original measurement. In various implementations, the system may modify the originally identified reception time based on the presence of the body. In some cases, the system may subtract a predetermined delay from the original reception time to generate the adjusted reception time. In various examples, the system may use the machine learning model to identify a delay associated with the specific signal pattern of the received wireless signal and may subtract the identified delay from the original reception time to generate the adjusted reception time.

At 608, the system may identify the location of the tag based on the adjusted measurement. For instance, the system may use the adjusted reception time to estimate the location of the tag in accordance with any of the techniques described herein.

Figure 6B:
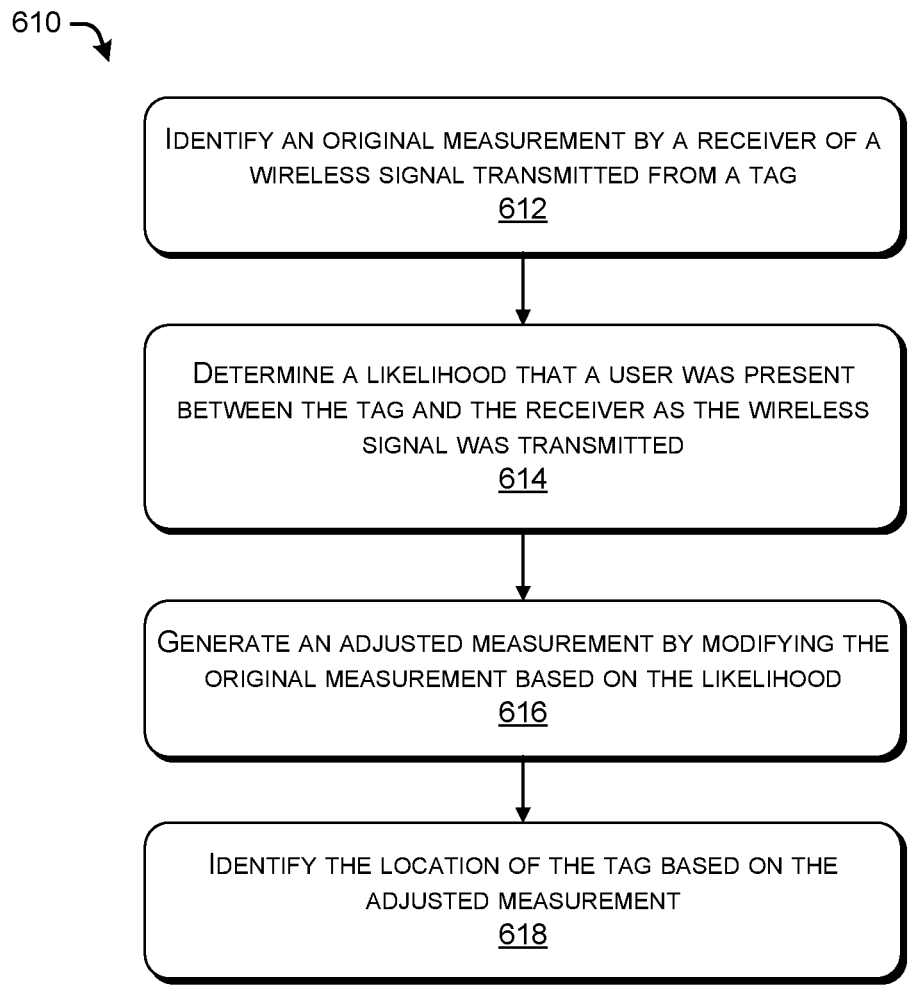

FIG. 6B illustrates an example process 610 for taking into account the position of a user in identifying the location of a tag in an environment. In some examples, the process 610 can be performed by a location system, such as the location system 808 described below with reference to FIGS. 8 to 10, the location engines 1006 or 1108 described below with reference to FIGS. 10 and 11, or any suitable RTLS.

At 612, the system may identify an original measurement by a receiver of a wireless signal transmitted from a tag. The original measurement may be a timing measurement, in some cases. For instance, the original measurement may be a time-of-flight between the tag and the receiver. In some cases, the original measurement can be a time at which the receiver received the wireless signal from the tag.

At 614, the system may determine a likelihood that a user of the tag was present between the tag and the receiver as the wireless signal was transmitted between the tag and the receiver. In some cases, the system may identify a positional relationship between the tag and the user. For instance, the tag may be predetermined to be attached, worn, or held by the user at a particular side of the user (e.g., front side, right side, left side, back side, or the like). Based on the positional relationship between the tag and the user, as well as the estimated positions of the tag and the receiver, the system can determine the likelihood. In some cases, for the purposes of identifying the estimated position of the tag, the system may presume that the tag is located at a previous location, or may estimate the position of the tag based on the original measurement generated by the receiver (without adjustment).

At 616, the system may generate an adjusted measurement by modifying the original measurement identified at 602 based on the likelihood. In some cases, the system may correct for the influence of the user's body on the original measurement. For instance, if the system determines that there is a high likelihood that the user was present between the tag and the receiver, the system may adjust the original measurement accordingly. However, if the system determines that there is a low likelihood that the user was present between the tag and the receiver, the system may refrain from significantly adjusting the original measurement.

At 618, the system may identify the location of the tag based on the adjusted measurement. Accordingly, the influence of the user's body on the measurement used to generate the location can be reduced and/or eliminated.

Figure 7:
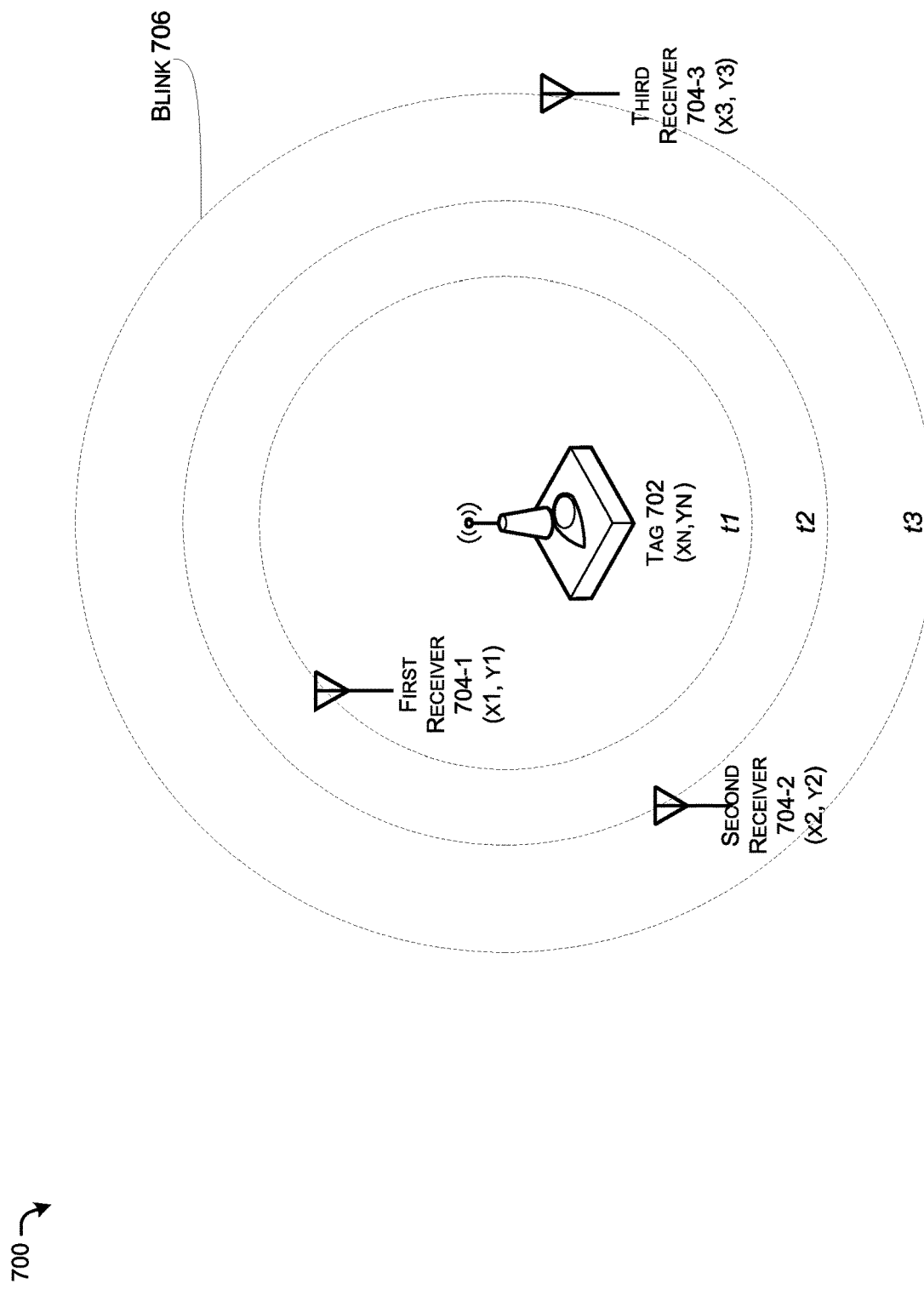
FIG. 7 illustrates an example location system environment.

FIG. 7 illustrates an example location system environment 700. As illustrated, the environment 700 includes a tag 702 and multiple receivers 704-1 to 704-3. In various implementations, the location system can be an RTLS. Various definitions of x, y, and t values used above are not necessarily applicable to the description below. For instance, the $(x_1, y_1)$, $(x_2, y_2)$, and $(x_3, y_3)$ positions described below may be different than the $(x_1, y_1)$, $(x_2, y_2)$, and $(x_3, y_3)$ positions described above with reference to FIGS. 1-6.

In various implementations, the tag 702 is configured to broadcast wireless signals. In some cases, the tag 702 may broadcast the wireless signals periodically. For instance, the tag 702 may be configured to broadcast the wireless signals at a frequency of once every five minutes, once a minute, twice a minute, once every ten seconds, once a second, multiple times per second, or the like. According to some examples in which the tag 702 is carried or affixed by a moving object or person, the tag 702 may broadcast the wireless signals at a frequency of once every 10-1000 milliseconds.

In some cases, the tag 702 may broadcast the wireless signals in response to an event. For instance, the tag 702 may broadcast the wireless signals in response to receiving a request for the wireless signals from another device, or in response to some other type of event. The wireless signals can be electromagnetic signals (e.g., infrared signals, radio signals, etc.), ultrasonic signals, subsonic signals, or the like.

The receivers 704-1 to 704-3 are configured to receive the wireless signals from the tag 702, and to recognize the times at which the wireless signals are received. The receivers 704-1 to 704-3 may be referred to as "anchors" in some cases. In various implementations, the receivers 704-1 to 704-3 are located at known positions. In some implementations, the receivers 704-1 to 704-3 may be mounted at fixed positions on walls, ceilings, or fixtures within a hospital building. The receivers 704-1 to 704-3 may be located at different positions. As illustrated in FIG. 7, a first receiver 704-1 may be located at position $(x_1, y_1)$, a second receiver 704-2 may be located at position $(x_2, y_2)$, and a third receiver 704-3 may be located at a position $(x_3, y_3)$. Although the environment 700 illustrated in FIG. 7 is depicted two dimensions, in some cases, the environment 700 can be defined in three dimensions.

In some cases, the receivers 704-1 to 704-3 may be further configured to communicate with each other over a wired (e.g., Ethernet, fiber-optic, etc.) and/or wireless (e.g., Wi-Fi, Bluetooth, etc.) Local Area Network (LAN).

In some implementations, a single wireless signal broadcast by the tag 702 may be referred to as a "blink." As depicted in FIG. 1, an example wireless signal broadcast or blink 706 is transmitted from the tag 702 at time=$t_0$. The blink 706 is received at the first receiver 704-1 at time=$t_1$, at the second receiver 704-1 at time=$t_2$, and at the third receiver 704-3 at time=$t_3$.

The position of the tag 702 may be derived based on the positions of the receivers 704-1 to 704-3 and the times at which the receivers 704-1 to 704-3 receive the blink 706. In various example implementations, the distances between the tag 702 and the receivers 704-1 to 704-3 may be calculated.

In some cases, the blink 706 indicates $t_0$. At least one of the receivers 704-1 to 704-3 may be able to derive $t_0$ from the blink 706. Accordingly, a time-of-flight of the blink 706 between the tag 702 and each one of the receivers 704-1 to 704-3 can be derived according to the following Formula 2:

$$\Delta t = t_n - t_0$$

wherein $\Delta t$ is the time-of-flight of the blink 706, $t_n$ is the time at which a receiver receives the blink 706 (e.g., $t_1$ for the first receiver 704-1, $t_2$ for the second receiver 704-2, and $t_3$ for the third receiver 704-3), and $t_0$ is the time at which the tag 702 transmits the blink 706.

Based on the times-of-flight of the blink 706 between the tag 702 and the receivers 704-1 to 704-3, distances between the tag 702 and the receivers 704-1 to 704-3 can be derived based on the following Formula 3:

$$d = \Delta t * v$$

wherein d is the distance between the tag 702 and a particular receiver, $\Delta t$ is the time-of-flight of the blink 706 between the tag 702 and the particular receiver, and v is the velocity of the blink 706. If the blink 706 is an electromagnetic signal, the velocity of the blink 706 can be estimated as the speed of light. If the blink 706 is an ultrasonic or subsonic signal, the velocity of the blink 706 can be estimated as the speed of sound (e.g., through ambient air).

Finally, the position of the tag 702 can be calculated based on the distances between the tag 702 and the receivers 704-1 to 704-3, as well as the known positions of the receivers 704-1 to 704-3. If the position of the tag 702 is defined as $(x_n, y_n)$, the following Formulas 4 can be used to derive the position of the tag 702, $$d_1^2 = (x_1 - x_n)^2 + (y_1 - y_n)^2$$

$$d_2^2 = (x_2 - x_n)^2 + (y_2 - y_n)^2$$

$$d_3^2 = (x_3 - x_n)^2 + (y_3 - y_n)^2$$

wherein $d_1$ is the distance between the first receiver 704-1 and the tag 702, $d_2$ is the distance between the second receiver 704-2 and the tag 702, $d_3$ is the distance between the third receiver 704-3 and the tag 702, $x_1$ is the position of the first receiver 704-1 on the x axis, $y_1$ is the position of the first receiver 704-1 on the y axis, $x_2$ is the position of the second receiver 704-2 on the x axis, $y_2$ is the position of the second receiver 704-2 on the y axis, $x_3$ is the position of the third receiver 704-3 on the x axis, and $y_3$ is the position of the third receiver 704-3 on the y axis.

In some implementations, $t_0$ may be unknown. In these cases, the position of the tag 702 can be derived by solving for $x_n$ and $y_n$ in the following Formulas 5:

$$(v(t_1 - t_0))^2 = (x_1 - x_n)^2 + (y_1 - y_n)^2$$

$$(v(t_2 - t_0))^2 = (x_2 - x_n)^2 + (y_2 - y_n)^2$$

$$(v(t_3 - t_0))^2 = (x_3 - x_n)^2 + (y_3 - y_n)^2$$

wherein $t_1$, is the time at which the first receiver 704-1 receives the blink 706, $t_2$ is the time at which the second receiver 704-2 receives the blink 706, $t_3$ is the time at which the third receiver 704-3 receives the blink 706, $t_0$ is the time at which the tag 702 transmits the blink 706, $x_1$ is the position of the first receiver 704-1 on the x axis, $y_1$ is the position of the first receiver 704-1 on the y axis, $x_2$ is the position of the second receiver 704-2 on the x axis, $y_2$ is the position of the second receiver 704-2 on the y axis, $x_3$ is the position of the third receiver 704-3 on the x axis, and $y_3$ is the position of the third receiver 704-3 on the y axis. Using Formulas 5 above, the $t_0$ term can be eliminated and the $x_n$ and $y_n$ terms can be derived.

In some implementations, one of the receivers 704-1 to 704-3 receives timing information from the other receivers. For instance, the first receiver 704-1 may receive a timing report indicating $t_2$ from the second receiver 704-2 and may receive a timing report indicating $t_3$ from the third receiver 704-3. In some cases, the receiver with the timing information calculates the position of the tag 702. In various examples, the receiver with the timing information forwards the timing information to a location system, which can calculate the location of the tag 702 using the timing information.

According to some implementations, individual receivers among the receivers 704-1 to 704-3 may have differently calibrated clocks. In some cases, each receiver 704-1 to 704-3 may estimate its reception time in its individual time base. To calibrate the different time bases, the first receiver 704-1 may transmit a synchronization signal to the second receiver 704-2 and the third receiver 704-3. The first receiver 704-1 may measure its transmission time ($t_4$) of the synchronization signal. The second receiver 704-2 may measure its reception time of the synchronization signal ($t_5$) and transmit an indication of the reception time to the first receiver 704-1. A first time-of-flight between the first receiver 704-1 and the second receiver 704-2 ($\Delta t_1$) may have been previously identified. The third receiver 704-3 may measure its reception time of the synchronization signal ($t_6$) and transmit an indication of the reception time to the first receiver. A second time-of-flight between the first receiver 704-1 and the third receiver 704-3 ($\Delta t_2$) may have been previously identified. In various implementations, an offset ($r_1$) between the time base of the first receiver 704-1 and the time base of the second receiver 704-2, as well as an offset ($r_2$) between the time base of the first receiver 704-1 and the time base of the third receiver 704-3, can be calculated according to the following Formulas 6:

$$r_1 = t_5 - (t_4 + \Delta t_1)$$

$$r_2 = t_6 - (t_4 + \Delta t_2)$$

In various implementations, the offsets $r_1$ and $r_2$ can be applied to any reception times reported by the second receiver 704-2 and the third receiver 704-3 to the first receiver 704-1, in order to ensure that $t_0$, $t_1$, $t_2$, $t_3$ are estimated in the same time base.

Figure 8:
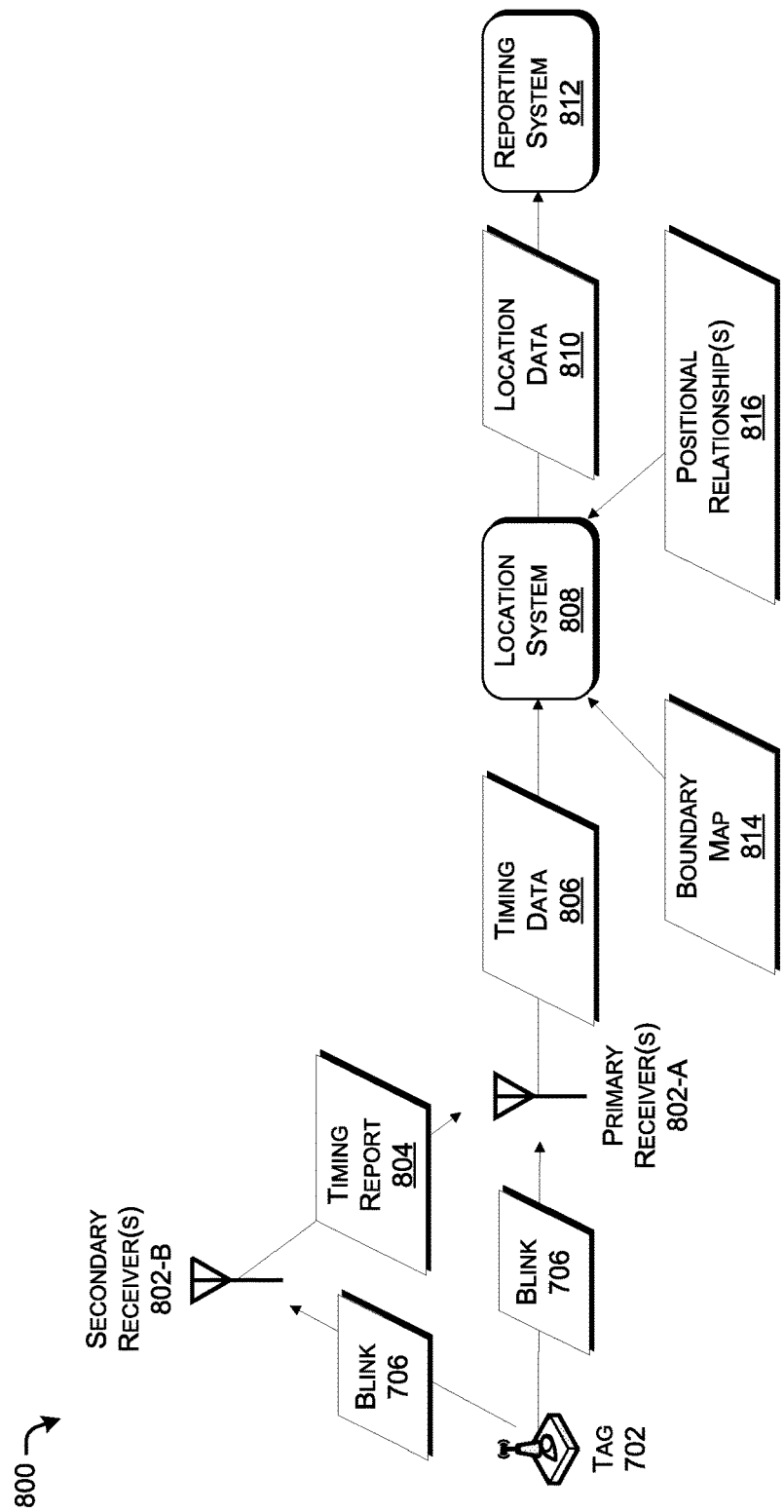
FIG. 8 illustrates an example environment for locating tags in a clinical environment.

FIG. 8 illustrates an example environment 800 for locating tags in a clinical environment. As illustrated, the environment 800 includes the tag 702 transmitting the blink 706, described above with reference to FIG. 7.

As illustrated in FIG. 8, the tag 702 transmits the blink 706 to multiple receivers 802-A and 802-B. In some implementations, the multiple receivers 802-A and 802-B can include the receivers 704-1 to 704-3 described above with reference to FIG. 7. The multiple receivers 802-A and 802-B include primary receiver(s) 802-A and secondary receiver(s) 802-B. The primary receiver(s) 802-A may be connected to the secondary receiver(s) 802-B over a wired and/or wireless Local Area Network (LAN). The secondary receiver(s) 802-B may be configured to identify time(s) when the blink 706 is received by the secondary receiver(s) 802-B and may inform the primary receiver(s) 802-A of the time(s) in a timing report 804. The timing report 804 may be transmitted over the LAN. The primary receiver(s) 802-A may be configured to identify time(s) when the blink 706 is received by the primary receiver(s) 802-A, identify time(s) when the blink 706 is received by the secondary receiver(s) 802-B based on the timing report 804, and may aggregate the times in timing data 806. The primary receiver(s) 802-A may transmit the timing data 806 to a location system 808. In some cases, the timing data 806 may indicate identifiers of the primary receiver(s) 802-A and the secondary receiver(s) 802-B along with the receipt times of the blink 706. In some examples, the timing data 806 may indicate the locations of the primary receiver(s) 802-A and the secondary receiver(s) 802-B along with the receipt times of the blink 706.

The location system 808 may be configured to identify the location of the tag 702 based on the timing data 806. In various implementations, the location system 808 can be a computer system including at least one processor configured to perform operations stored in memory. In some cases, the location system 808 may be able to identify the locations of the primary receiver(s) 802-A and the secondary receiver(s) 802-B by cross-referencing identifiers of the primary receiver(s) 802-A and the secondary receiver(s) 802-B in a database. The identifiers of the primary receiver(s) 802-A and the secondary receiver(s) 802-B may be included in the timing data 806. In some cases, the locations of the primary receiver(s) 802-A and the secondary receiver(s) 802-B may be indicated in the timing data 806 itself.

In various implementations, the location system 808 may be configured to identify the locations of multiple tags including the tag 702. To distinguish the timing data 806 associated with the tag 702 from other timing data associated with other tags, the primary receiver(s) 802-A may generate the timing data 806 indicate the identifier of the tag 702.

Once the location system 808 identifies the location of the tag 702, the location system 808 may indicate the location in location data 810. In some cases, the location data 810 may also indicate the identifier of the tag 702. The location system 808 may transmit the location data 810 to a reporting system 812. The reporting system 812 may output the location of the tag 702 and/or take various other actions based on the location of the tag 702. For instance, if the tag 702 is associated with a care provider and the reporting system 812 determines that the tag 702 is located within the vicinity of a patient in need of immediate care, the reporting system 812 may selectively notify the care provider of the patient's need and request that the care provider attend to the patient.

In various implementations, at least one of the location system 808 and the reporting system 812 may be located outside of an internal network within the clinical environment. At least one firewall may be disposed between the primary receiver(s) 802-A and the location system 808, within the location system 808, between the location system 808 and the reporting system 812, or within the reporting system 812. Accordingly, a security policy within the clinical environment can be enforced.

In various implementations, a boundary map 814 may be utilized by the location system 808 to correct the locations the location system 808 calculates based on the timing data 806. In addition, positional relationship(s) 816 (e.g., between the tag 702 and a user associated with the tag 702) can be utilized by the location system 808 to correct the locations the location system 808 calculates. In some cases, the boundary map 814 and/or the positional relationship(s) 816 can be stored in a local memory of a device implementing the location system 808.

Figure 9:
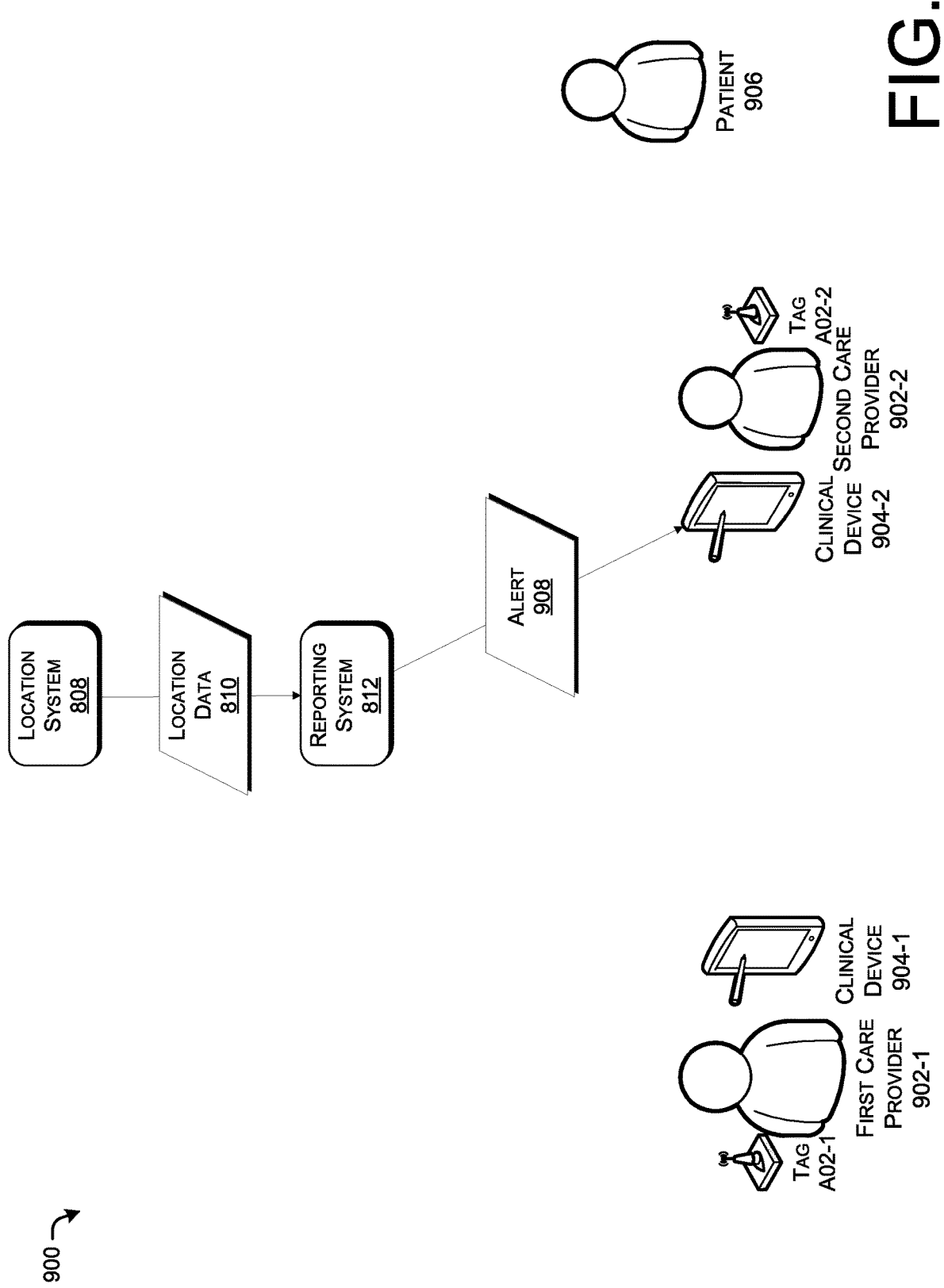
FIG. 9 illustrates an example environment of a location system being utilized in a clinical environment.

FIG. 9 illustrates an example environment 900 of a location system 808 being utilized in a clinical environment. As noted above, the location system 808 may provide the reporting system 812 with the location data 810. The location data 810 may indicate the locations of various tags (e.g., tag 702) throughout the clinical environment. In the example illustrated in FIG. 9, the location data 810 may indicate the locations of first and second tags 702-1 and 702-2 in the clinical environment.

First tag 702-1 may be worn by, held by, or attached to clinical provider 902-1. Clinical provider 902-1 may be associated with a clinical device 904-1. The clinical device 904-1 may be a mobile device, in some cases. In various implementations, the clinical device 904-1 could output alerts, instructions, or the like, to assist the clinical provider 902-1 with treating and monitoring patients within the clinical environment.

Similarly, second tag 702-2 may be worn by, held by, or attached to clinical provider 902-2. Clinical provider 902-2 may be associated with a clinical device 904-2. The clinical device 904-2 may be a mobile device, in some cases. In various implementations, the clinical device 904-2 could output alerts, instructions, or the like, to assist the clinical provider 902-2 with treating and monitoring patients within the clinical environment.

In various implementations, the reporting system 812 may identify that a patient 906 is in need of assistance from a clinical provider, such as either one of clinical providers 902-1 or 902-2. For example, the reporting system 812 may identify that the patient 906 is in need of non-emergency care (e.g., changing of a wound dressing, drug administration, or the like) or emergency care (e.g., defibrillation, tracheostomy, or the like). The reporting system 812 may also be aware of the location of the patient 906.

In some instances, the reporting system 812 may compare the location data 810 to the location of the patient to identify which one of the tags 702-1 or 702-2 is closest to the patient 906. Based on this comparison, the reporting system 812 may identify that the tag 702-2 is closest to the patient 906. In some cases, the reporting system 812 may identify that the tag 702-2 associated with the second care provider 902-2 is within a predetermined distance of the patient 906. According to various examples, the reporting system 812 may determine that the tag 702-2 is within the same room as the patient 906, is within a predetermined distance (e.g., 10 feet, 20 feet, etc.) of the patient, is the closest available care provider to the patient 906, or the like.

The reporting system 812 may identify that the tag 702-2 is associated with the second care provider 902-2 and/or the clinical device 904-2 utilized by the second care provider 902-2. The reporting system 812 can selectively transmit an alert 908 to the clinical device 904-2. In response to receiving the alert, the clinical device 904-2 may output an instruction to provide assistance to the patient 906.

Figure 10:
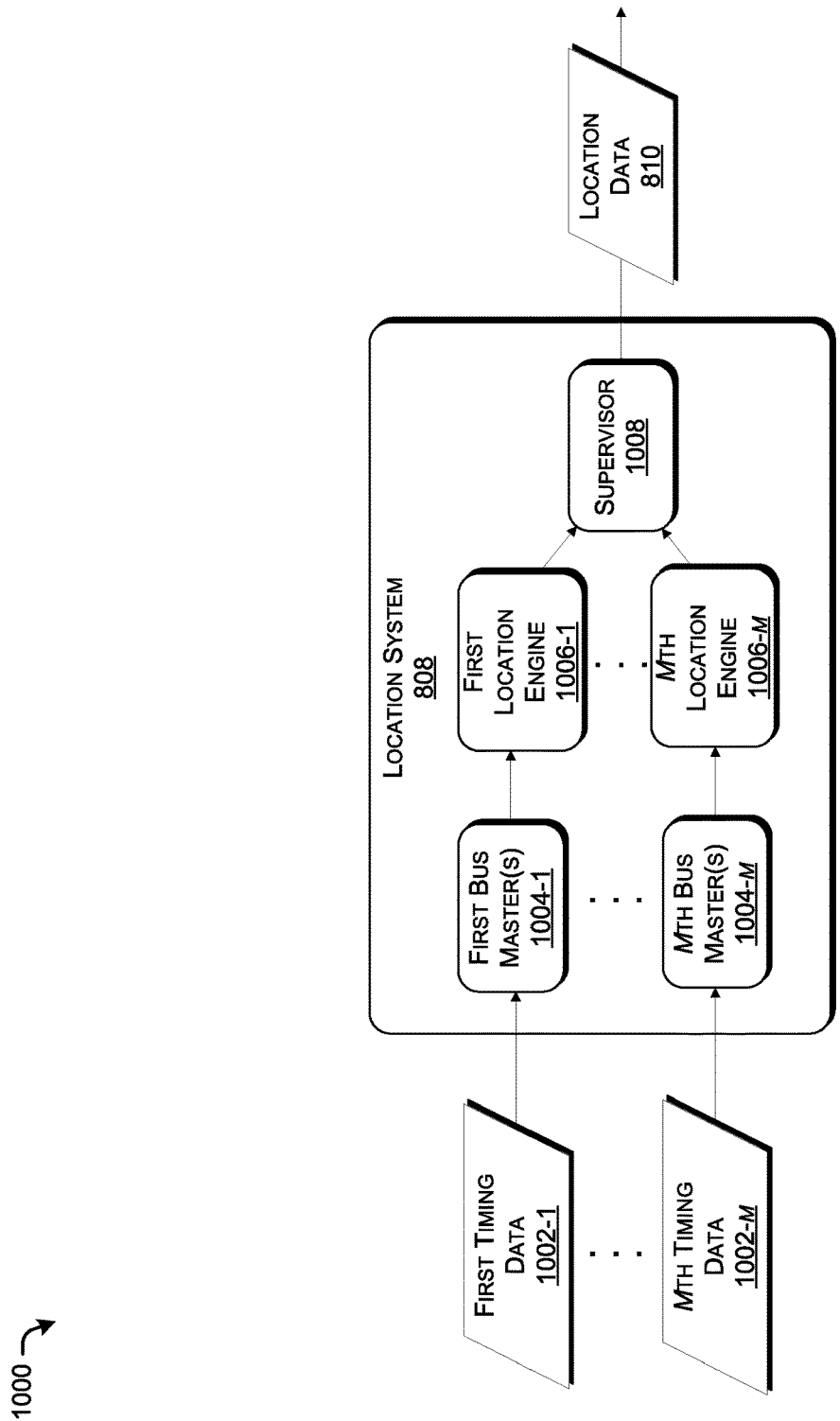
FIG. 10 illustrates an example environment for determining the locations of multiple tags in a clinical environment.

FIG. 10 illustrates an example environment 1000 for determining the locations of multiple tags in a clinical environment. As illustrated, the environment 1000 includes the location system 808 and the location data 810 described above with reference to FIG. 8.

First through mth timing data 1002-1 to 1002-m may be received at first to mth bus masters 1004-1 to 1004-m in the location system 808. The timing data 1002-1 to 1002-m may represent timing data from multiple receivers receiving signals from multiple tags in the clinical environment. For instance, first timing data 1002-1 may represent timing data from multiple primary receivers based on blinks from multiple tags. In some cases, the timing data 1002-1 to 1002-m can be represented in data streams transferred from the primary receivers to the first to mth bus masters 1004-1 to 1004-m.

The bus masters 1004-1 to 1004-m may each include hardware and/or software including a serial connection to which multiple receivers (e.g., multiple primary receivers) are connected. In various implementations, the bus masters 1004-1 to 1004-m may be configured to orchestrate communications between the multiple receivers and other network nodes within the location system 808. In some cases, the bus masters 1004-1 to 1004-m are connected to other network nodes within the location system 808 via a Local Area Network (LAN).

In some cases, the bus masters 1004-1 to 1004-m may generate individual data packets associated with single blink events (e.g., the same blink from the same tag) and transmit the individual data packets to the location engines 1006-1 to 1006-*m*. When the bus masters 1004-1 to 1004-*m* receive timing data 1002-1 to 1002-*m* from multiple primary receivers based on the same blink event, the bus masters 1004-1 to 1004-*m* may be able to aggregate the subset of the timing data 1002-1 to 1002-*m* from the same blink event into individual data packets.

The locating engines 1006-1 to 1006-*p* may be configured to calculate the locations of the tags based on the data received from the bus masters 1004-1 to 1004-*m*. In some cases, p<m, such that there is a greater number of bus masters 1004-1 to 1004-*m* than locating engines 1006-1 to 1006-*p*. For instance, multiple bus masters 1004-1 to 1004-*m* may be connected to a single one of the locating engines 1006-1 to 1006-*p*.

A single supervisor (also referred to as an "aggregator") 1008 may receive indications of the calculated locations from the location engines 1006-1 to 1006-*p*. The single supervisor 1008 may aggregate the locations into location data 810. The location data 810 may be in the form of a data stream indicating individual tags and their calculated locations.

According to various implementations, one or more of the bus masters 1004-1 to 1004-*m*, locating engines 1006-1 to 1006-*p*, and aggregator 1008 may be network nodes.

Figure 11:
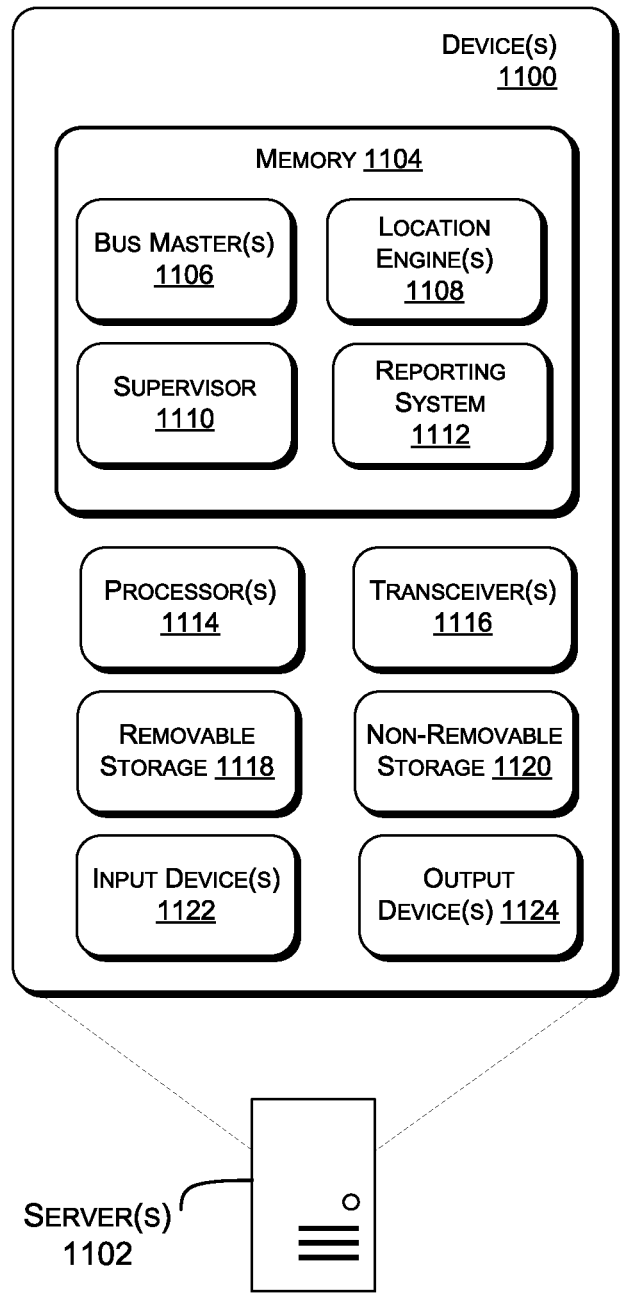
FIG. 11 illustrates at least one example device configured to enable and/or perform the some or all of the functionality discussed herein.

FIG. 11 illustrates at least one example device 1100 configured to enable and/or perform the some or all of the functionality discussed herein. Further, the device(s) 1100 can be implemented as one or more server computers 1102, a network element on a dedicated hardware, as a software instance running on a dedicated hardware, or as a virtualized function instantiated on an appropriate platform, such as a cloud infrastructure, and the like. It is to be understood in the context of this disclosure that the device(s) 1100 can be implemented as a single device or as a plurality of devices with components and data distributed among them.

As illustrated, the device(s) 1100 comprise a memory 1104. In various embodiments, the memory 1104 is volatile (including a component such as Random Access Memory (RAM)), non-volatile (including a component such as Read Only Memory (ROM), flash memory, etc.) or some combination of the two.

The memory 1104 may include various components, such as at least one bus master 1106, at least one location engine 1108, a supervisor 1110, a reporting system 1112, and the like. Any of the bus master(s) 1106, the location engine(s) 1108, the supervisor 1110, and the reporting system 1112 can comprise methods, threads, processes, applications, or any other sort of executable instructions. The bus master(s) 1106, the location engine(s) 1108, the supervisor 1110, and the reporting system 1112 and various other elements stored in the memory 1104 can also include files and databases.

The memory 1104 may include various instructions (e.g., instructions in the bus master(s) 1106, location engine(s) 1108, supervisor 1110, and/or reporting system 1112), which can be executed by at least one processor 1114 to perform operations. In some embodiments, the processor(s) 1114 includes a Central Processing Unit (CPU), a Graphics Processing Unit (GPU), or both CPU and GPU, or other processing unit or component known in the art.

The device(s) 1100 can also include additional data storage devices (removable and/or non-removable) such as, for example, magnetic disks, optical disks, or tape. Such additional storage is illustrated in FIG. 11 by removable storage 1118 and non-removable storage 1120. Tangible computer-readable media can include volatile and nonvolatile, removable and non-removable media implemented in any method or technology for storage of information, such as computer readable instructions, data structures, program modules, or other data. The memory 1104, removable storage 1118, and non-removable storage 1120 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1100. Any such tangible computer-readable media can be part of the device(s) 1100.

The device(s) 1100 also can include input device(s) 1122, such as a keypad, a cursor control, a touch-sensitive display, voice input device, etc., and output device(s) 1124 such as a display, speakers, printers, etc. These devices are well known in the art and need not be discussed at length here. In particular implementations, a user can provide input to the device(s) 1100 via a user interface associated with the input device(s) 1122 and/or the output device(s) 1124.

As illustrated in FIG. 11, the device(s) 1100 can also include one or more wired or wireless transceiver(s) 1116. For example, the transceiver(s) 1116 can include a Network Interface Card (NIC), a network adapter, a Local Area Network (LAN) adapter, or a physical, virtual, or logical address to connect to the various base stations or networks contemplated herein, for example, or the various user devices and servers. To increase throughput when exchanging wireless data, the transceiver(s) 1116 can utilize Multiple-Input/Multiple-Output (MIMO) technology. The transceiver(s) 1116 can include any sort of wireless transceivers capable of engaging in wireless, Radio Frequency (RF) communication. The transceiver(s) 1116 can also include other wireless modems, such as a modem for engaging in Wi-Fi, WiMAX, Bluetooth, or infrared communication.

In some implementations, the transceiver(s) 1116 can be used to communicate between various functions, components, modules, or the like, that are comprised in the device(s) 1100. For instance, the transceivers 1116 may facilitate communications between the bus master(s) 1106, the location engine(s) 1108, the supervisor 1110, and/or the reporting system 1112.

Figure 12:
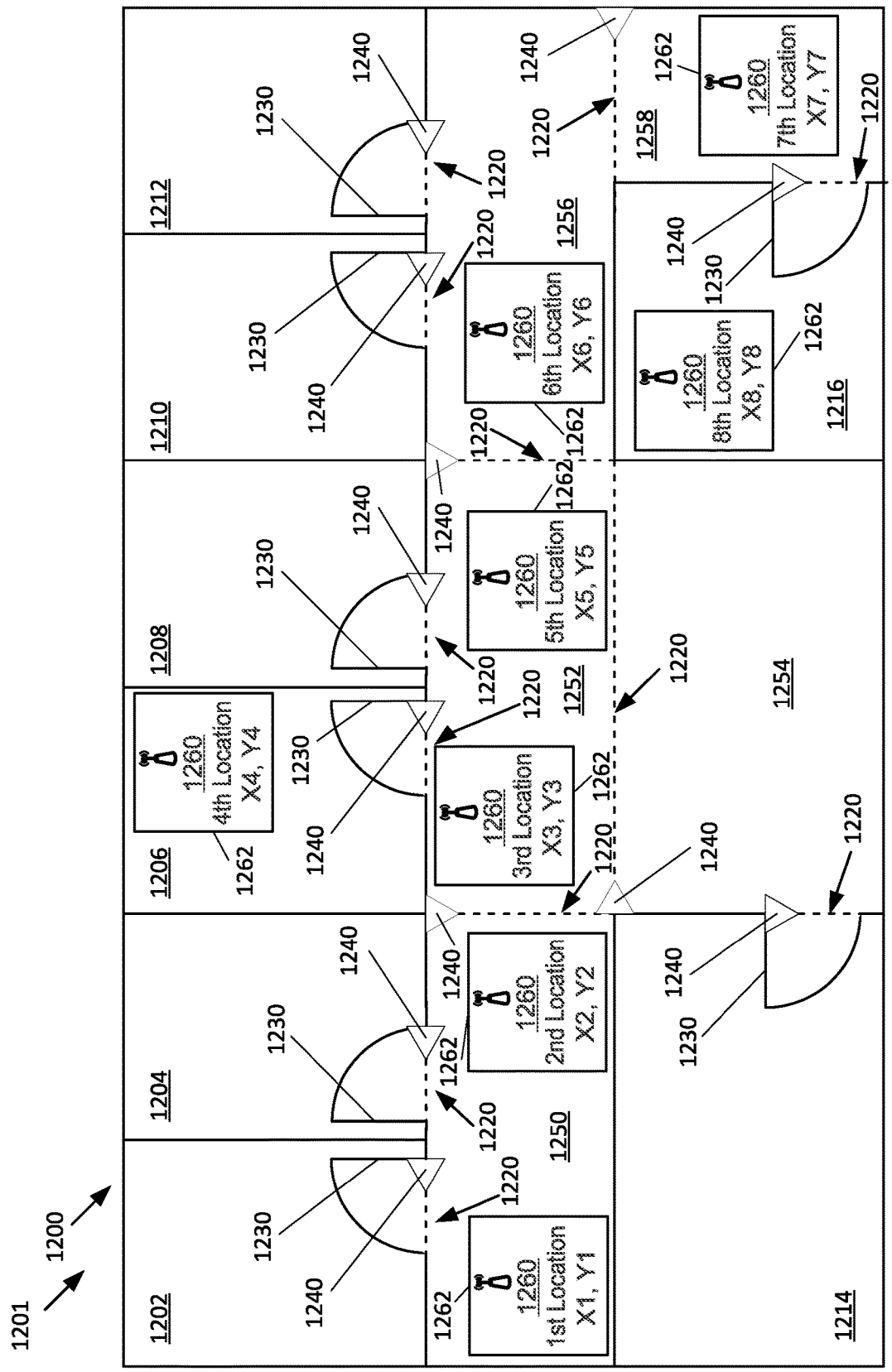
FIG. 12 illustrates a location system included in an example environment.

FIG. 12 illustrates an example environment 1201 that includes a location system 1200. The location system 1200 improves location detection accuracy by determining whether an asset has crossed a threshold between a previously detected area and a newly detected area. In some examples, the location system 1200 can be used in combination with the location systems described above. Alternatively, the location system 1200 can be used separately.

A tag, such as one of the tags described above, can have an error range which causes a difference (e.g., tolerance) between the detected location of the tag and the actual location of the tag. In some examples, the error range can be up to one meter in radius. Due to the error range of the tag, it is sometimes not possible to determine whether an asset associated with the tag has left a previously detected area to enter a newly detected area when the asset and tag are next to a threshold between the previously detected area and the newly detected area. The location system 1200 overcomes this challenge by using a plurality of detection devices 1240 that detect the passage of an asset through a threshold such as a doorway or hallway segment.

In the example environment 1201, a tag 1260 is associated with an asset 1262. As described above, the asset 1262 can be an object (e.g., a medical device, a hospital bed, or the like), and the tag 1260 is attached to the object. In other instances, the asset 1262 is a person (e.g., a patient, care provider, or the like), and the tag 1260 is worn by the person. In some examples, the tag 1260 is worn on a lanyard or necklace, or is integrated into a wristband worn by the person, or is integrated into clothes worn by the person.

The example environment 1201 is a floor plan that has a plurality of rooms (e.g., rooms 1202, 1204, 1206, 1208, 1210, 1212, 1214, and 1216). Each room is defined by boundaries such as walls and the like. Solid objects, such as the asset 1262, cannot pass through these boundaries. Additionally, each room includes at least one threshold 1220. As described above, the term "threshold" may refer to a doorway, a gate, an opening, a window, or any other permeable boundary that can be traversed by solid objects. In the example illustrated in FIG. 12, the thresholds 1220 in the rooms 1202-1216 are doorways, in which doors 1230 provide open access to the rooms 1202-1216 when opened and prevent open access when closed.

In addition to the thresholds 1220 for the rooms 1202-1216, the example environment 1201 also includes thresholds 1220 between hallway segments 1250, 1252, 1254, 1256, and 1258. The thresholds 1220 between the hallway segments 1250-1258 are traversed by an object such as a person when walking through the hallway to visit one or more of the rooms 1202-1216.

The detection devices 1240 detect the passage of the asset 1262 through the thresholds 1220 between the rooms and hallway segments. In some examples, the detection devices 1240 are positioned on all doorways and hallway segments in the example environment 1201. In other examples, the detection devices 1240 are positioned on only a select number of doorways and hallway segments such as those bordering one or more areas of particular interest.

Each detection device 1240 is associated with a particular doorway or hallway segment within the example environment 1201. For example, a detection device 1240 can be associated with a threshold 1220 of room 1202, another detection device 1240 can be associated with a threshold 1220 of room 1204, and so on. Similarly, a detection device 1240 can be associated with a threshold 1220 between hallway segments 1250 and 1252, another detection device 1240 can be associated with a threshold 1220 between hallway segments 1252 and 1254, and so on. In some examples, each detection device 1240 includes a unique identifier that is paired to a threshold 1220 of a particular room or hallway segment to associate the detection device 1240 with that particular room or hallway segment in the example environment 1201.

The location of the tag 1260 in the example environment 1201 can be estimated using one or more of the techniques described above. The location of the tag 1260 can be estimated as an X,Y coordinate within a two-dimensional floor plan of the example environment 1201. As an illustrative example, the tag 1260 is estimated by the location system 1200 to be in a first location identified by coordinates X1, Y1 in the hallway segment 1250. Thereafter, the tag 1260 is estimated by the location system 1200 to be in a second location identified by coordinates X2, Y2 in the hallway segment 1250. As shown in FIG. 12, both the first and second locations are in the hallway segment 1250 such that the tag 1260 and asset 1262 have not passed through a threshold 1220 between the hallway segment 1250 and another hallway segment or room.

In continuing with this illustrative example, the tag 1260 is estimated by the location system 1200 to be in a third location identified by coordinates X3, Y3 in the hallway segment 1252. Thus, the tag 1260 and asset 1262 are determined to have left the hallway segment 1250 (i.e., the second location X2, Y2) and to have entered the hallway segment 1252 (i.e., the third location X3, Y3). The location system 1200 confirms the estimated third location X3, Y3 by determining whether a transition event is detected by the detection device 1240 positioned in the threshold 1220 between the hallway segments 1250, 1252.

The detection device 1240 detects the transition event by sensing an object such as the asset 1262 passing through the threshold 1220 between the hallway segments 1250, 1252. When a signal from the detection device 1240 detects that the asset 1262 passed through the threshold 1220 between the hallway segments 1250 and 1252, a transition event is detected such that the estimate of the third location X3, Y3 is confirmed. When the signal from the detection device 1240 does not detect that the asset 1262 passed through the threshold 1220 between the hallway segments 1250 and 1252, a transition event is not detected and the estimate of the third location X3, Y3 is adjusted. In some examples, the estimate of the third location X3, Y3 is adjusted by the location system 1200 to be on the same side of the threshold 1220 as the last known location of the tag 1260 and asset 1262 (i.e., the second location X2, Y2 in the hallway segment 1250) since it is likely that the error range of the tag 1260 caused an incorrect estimate for the third location X3, Y3 of the tag 1260 and asset 1262.

Still referring to the example illustrated in FIG. 12, the tag 1260 is estimated by the location system 1200 to be in a fourth location identified by coordinates X4, Y4 in the room 1206. Thus, the tag 1260 is determined to have left the hallway segment 1252 (i.e., the third location X3, Y3) and to have entered the room 1206 (i.e., the fourth location X4, Y4). In this example, the location system 1200 confirms the estimated fourth location X4, Y4 by determining whether a transition event is detected by a detection device 1240 positioned in the threshold 1220 between the hallway segment 1252 and room 1206.

When a signal from the detection device 1240 detects that the asset 1262 passed through the threshold 1220 between the hallway segment 1252 and room 1206, the estimate of the fourth location X4, Y4 is confirmed. When the signal from the detection device 1240 does not detect that the asset 1262 passed through the threshold 1220 between the hallway segment 1252 and room 1206, the estimate of the fourth location X4, Y4 is adjusted. In some examples, the estimate of the fourth location X4, Y4 is adjusted by the location system 1200 to be on the same side of the threshold 1220 as the last known location of the tag 1260 and asset 1262 (i.e., the third location X3, Y3 in the hallway segment 1252) since it is likely that the error range of the tag 1260 caused an incorrect estimate for the fourth location X4, Y4. Accordingly, an estimated location for the tag 1260 and asset 1262 that transitions a threshold from one hallway segment 1250-1258 to another, or from a hallway segment 1250-1258 to a room 1202-1216, or from a room 1202-1216 to a hallway segment 1250-1258, is not permitted unless a transition event is detected by a detection device 1240 located in that threshold.

Furthermore, the transition events detected by the detection devices 1240 can help to confirm that the asset 1262 is in a particular room when the thresholds 1220 (i.e., doorways) for adjacent rooms are located side-by-side. For example, a transition event detected by the detection device 1240 positioned in the threshold 1220 between the room 1206 and hallway segment 1252 not only confirms that the asset 1262 is located in room 1206, but also that the asset 1262 is not located in the adjacent room 1208. Additionally, the lack of a transition event detected by the detection device 1240 positioned in the threshold 1220 between the room 1208 and hallway segment 1252 confirms that the asset 1262 is not located in the adjacent room 1208.

Still referring to the example illustrated in FIG. 12, the location system 1200 can estimate a fifth location of the tag 1260 identified by coordinates X5, Y5 in the hallway segment 1252 such that the tag 1260 is determined to have left the room 1206 (i.e., the fourth location X4, Y4) and to have re-entered the hallway segment 1252 (i.e., the fifth location X5, Y5). Thereafter, the location system 1200 may estimate a sixth location of the tag 1260 identified by coordinates X6, Y6 in the hallway segment 1256, a seventh location of the tag 1260 identified by coordinates X7, Y7 in the hallway segment 1258, and an eighth location of the tag 1260 identified by coordinates X8, Y8 in room 1216. Each time the estimated location of the tag 1260 and asset 1262 is determined to have crossed a threshold 1220 in the example environment 1201, the location system 1200 uses a detection device 1240 to confirm whether the tag 1260 and asset 1262 did indeed cross the threshold 1220 to confirm the estimated location of the tag 1260 and asset 1262 or adjust the location of the tag 1260 and asset 1262. In this manner, the movement of the tag 1260 and asset 1262 can be tracked as the tag 1260 and asset 1262 move between the various rooms 1202-1216 and hallway segments 1250-1258 in the example environment 1201.

Figure 13:
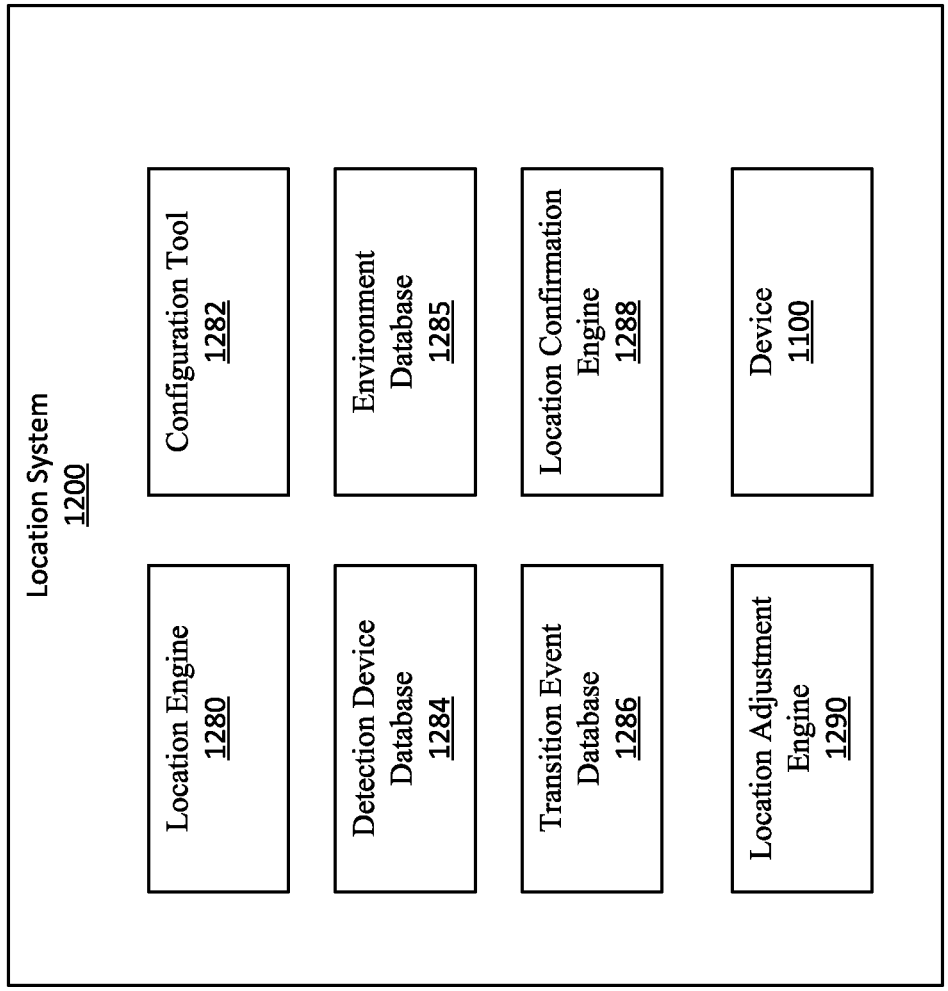
FIG. 13 schematically illustrates an example location system.

FIG. 13 schematically illustrates the location system 1200. Referring now to FIG. 13, the location system 1200 includes a location engine 1280, a configuration tool 1282, detection device database 1284, environment database 1285, a transition event database 1286, a location confirmation engine 1288, a location adjustment engine 1290, and at least one example device 1100 described above with reference to FIG. 11. In some further example embodiments, the location system 1200 includes additional or fewer components.

The location engine 1280 estimates the location of the tag 1260 in the example environment 1201 using one or more of the techniques described above. For example, the location engine 1280 can estimate the location of the tag 1260 by performing trilateration, multilateration, triangulation, and the like. The location engine 1280 can determine time lags of the wireless signals transmitted between the tag 1260 and various receivers associated with the location system 1200 based on the transmission times and the reception times, and can determine the distances between the tag 1260 and the receivers by multiplying the time lags by the velocity of the wireless signals. The location of the tag 1260 can be estimated based on differences between reception times of the same wireless signal by different receivers. Additional techniques for estimating the location of the tag 1260 are contemplated.

The configuration tool 1282 associates each detection devices 1240 with a particular threshold 1220 in the example environment 1201. For example, the configuration tool can associate a detection device 1240 with a threshold 1220 of the room 1202, can associate another detection device 1240 with a threshold 1220 of the room 1204, can associate a detection device 1240 with a threshold 1220 between the hallway segments 1250 and 1252, and so on. In some examples, each detection device 1240 has a unique identifier stored in the detection device database 1284. Similarly, data identifying the locations of the boundaries and thresholds in the example environment 1201 can be stored in the environment database 1285. The configuration tool 1282 correlates the unique identifier of each detection device 1240 to the location of the threshold 1220 where each detection device 1240 is positioned such that the location system 1200 knows the location of each detection device 1240 in the example environment 1201.

The transition event database 1286 receives and stores transition events from the detection devices 1240. For example, the transition event database 1286 receives and stores a transition event from a detection device 1240 positioned in a threshold 1220 when the asset 1262 crosses the threshold 1220 to enter or leave a hallway segment or room. In some examples, the transition events received in the transition event database 1286 are time stamped.

The location confirmation engine 1288 determines whether the location estimate from the location engine 1280 indicates that the asset 1262 has moved from one hallway segment 1250-1258 to another hallway segment, or whether the asset 1262 has moved from a hallway segment 1250-1258 to a room 1202-1216, or from a room 1202-1216 to a hallway segment 1250-1258. When location confirmation engine 1288 determines that the asset 1262 has moved into a new hallway segment 1250-1258, or has entered or left a room 1202-1216, the location confirmation engine 1288 determines whether a transition event is received in the transition event database 1286 from a detection device 1240 positioned in the appropriate threshold 1220 where the movement of the asset 1262 is estimated to have occurred.

When a transition event is received from a detection device 1240 positioned in the appropriate threshold 1220, the location estimate for the asset 1262 is confirmed. When the transition event is not received from a detection device 1240 positioned in the appropriate threshold 1220, the location estimate is adjusted by the location adjustment engine 1290.

In some examples, the time stamp of the transition event is compared to a minimum time allowance to determine whether the transition event is recent. If the time stamp indicates that the transition event from a detection device 1240 positioned in the appropriate threshold 1220 is not recent, the transition event is discarded and/or ignored by the location confirmation engine 1288 such that the location estimate is adjusted by the location adjustment engine 1290.

The location adjustment engine 1290 adjusts the estimated location of the tag 1260 and asset 1262 when the estimated location is not confirmed by the location confirmation engine 1288. As an example, the location adjustment engine 1290 adjusts the estimated location to be on the same side of the threshold 1220 as the last known estimated location of the tag 1260 and asset 1262. Thus, an estimated location that indicates that the tag 1260 and asset 1262 have moved from one hallway segment 1250-1258 to another hallway segment, or from a hallway segment 1250-1258 to a room 1202-1216, or from a room 1202-1216 to a hallway segment 1250-1258, is not permitted by the location system 1200 unless a transition event is detected by a detection device 1240 positioned in the appropriate threshold 1220 to confirm the movement of the tag 1260 and asset 1262 to the new location within the example environment 1201.

Figure 14:
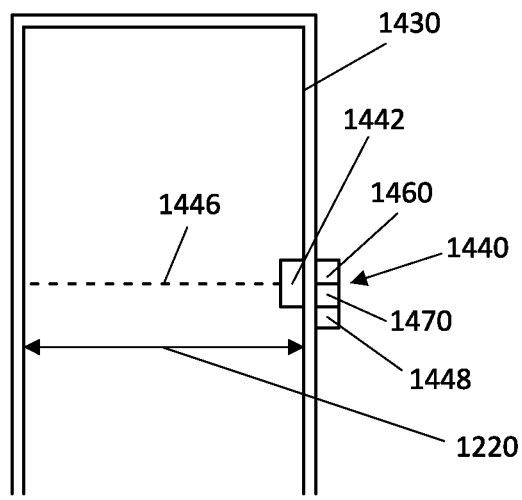
FIG. 14 illustrates a front view of a detection device, in accordance with a first embodiment, positioned on an example doorframe.

FIG. 14 illustrates a front view of a detection device 1440, in accordance with a first embodiment, positioned on an example doorframe 1430. The doorframe 1430 defines a threshold 1220 for a room 1202-1216 in the example environment 1201. While the detection device 1440 is illustrated in FIG. 14 with respect to the doorframe 1430, the detection device 1440 can also be positioned next to one or more walls that define a threshold 1220 between hallway segments 1250-1258 within the example environment 1201.

In this first embodiment, the detection device 1440 is a range finder that includes a signal generator 1442 that generates a signal 1446. The signal 1446 can be a light signal (e.g., laser, infra-red light, visible light, etc.), a sound signal (e.g., ultrasonic sound waves), and the like. The signal generator 1442 is installed on one side of the doorframe 1430, and uses the signal 1446 to measure a distance to an opposite side of the doorframe 1430. When the signal generator 1442 detects a decrease in the distance due to an object such as the asset 1262 passing through the doorframe 1430, the detection device 1440 detects a transition event.

In this embodiment, the detection device 1440 can be positioned either on a side of the doorframe 1430 such as where a door 1230 (see FIG. 12) is hinged, or alternatively, on a side of the doorframe 1430 opposite that of the hinges. In some examples, the detection device 1440 includes a temperature and humidity sensor 1448 to increase the accuracy of the range finder.

Figure 15:
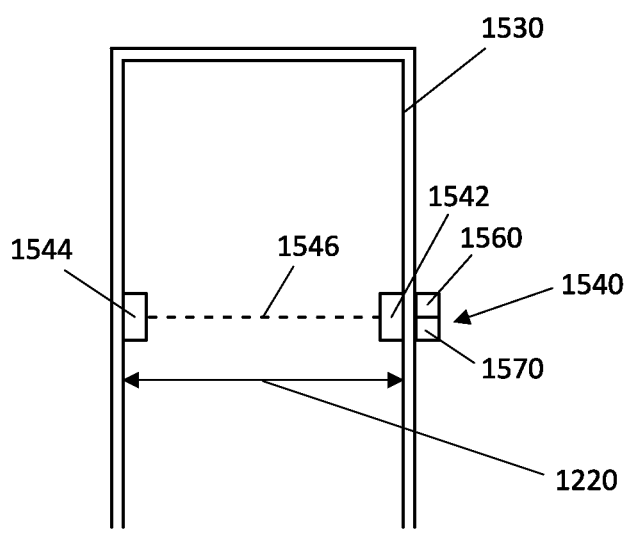
FIG. 15 illustrates a front view of a detection device, in accordance with a second embodiment, positioned on an example doorframe.

FIG. 15 illustrates a front view of a detection device 1540, in accordance with a second embodiment, positioned on an example doorframe 1530. While the detection device 1540 is illustrated in FIG. 15 with respect to the doorframe 1530, the detection device 1540 can also be positioned on one or more walls that define a threshold 1220 between hallway segments 1250-1258 within the example environment 1201.

In this second embodiment, the detection device 1540 includes both a signal generator 1542 and a signal receiver 1544. The signal generator 1542 may be substantially similar to the signal generator 1442 described above with reference to FIG. 14. The signal generator 1542 continuously transmits a signal 1546 across the threshold 1220, defined by the width of the doorframe 1530, for reception by the signal receiver 1544. When a solid object such as the asset 1262 passes through the doorframe 1530, the signal 1546 from the signal generator 1542 to the signal receiver 1544 is interrupted, and a transition event is detected.

In this embodiment, the position of the signal generator 1242 relative to the signal receiver 1244 can be alternated such that the signal generator 1542 can be positioned on a side of the doorframe 1530 where the door 1230 (see FIG. 12) is hinged, or alternatively can be positioned on a side of the doorframe 1530 opposite that of the hinges. Similarly, the signal receiver 1544 can be positioned on a side of the doorframe 1530 where a door jamb is located, or can be positioned on an opposite the side of the doorframe 1530 where the door 1230 is hinged.

Referring now to both embodiments of the detection devices 1440, 1540 described above with reference to FIGS. 14 and 15, the detection devices 1440, 1540 include a single-board microcontroller 1460, 1560.

Additionally, the detection devices 1440, 1540 include one or more wired or wireless communications devices 1470, 1570 to transmit the transition event to the location system 1200. The communications devices 1470, 1570 can include wireless transceivers to provide wireless communications including Bluetooth, Wi-Fi, WiMAX, or infrared communications. In some examples, the communications devices 1470, 1570 include a power over Ethernet bus that the detection devices 1440, 1540 plug into for both receiving power and transmitting the transition event to the location system 1200. In some examples, the detection devices 1440, 1540 transmit the transition event over the communications devices 1470, 1570 along with a time stamp to indicate when the transition event was detected by the detection devices 1440, 1540.

In some examples, the transition event is not associated with or correlated to the tag 1260 or asset 1262. In other examples, the signal 1446, 1546 can trigger an RFID event that associates the tag 1260 and asset 1262 with the transition event.

In some examples, the detection devices 1440, 1540 are battery powered. In other examples, the detection devices 1440, 1540 are powered by the power-over-Ethernet bus.

Various techniques can be used to attach the detection devices 1440, 1540 to the doorframes 1430, 1530. For example, the detection devices 1440, 1540 can be mounted directly onto the doorframes 1430, 1530. Alternatively, the detection devices 1440, 1540 can be mounted onto a wall next to the doorframe 1430, 1530 and angled toward an opposite side of the doorframe 1430, 1530 to transmit and/or receive the signals 1446, 1546.

Figure 16:
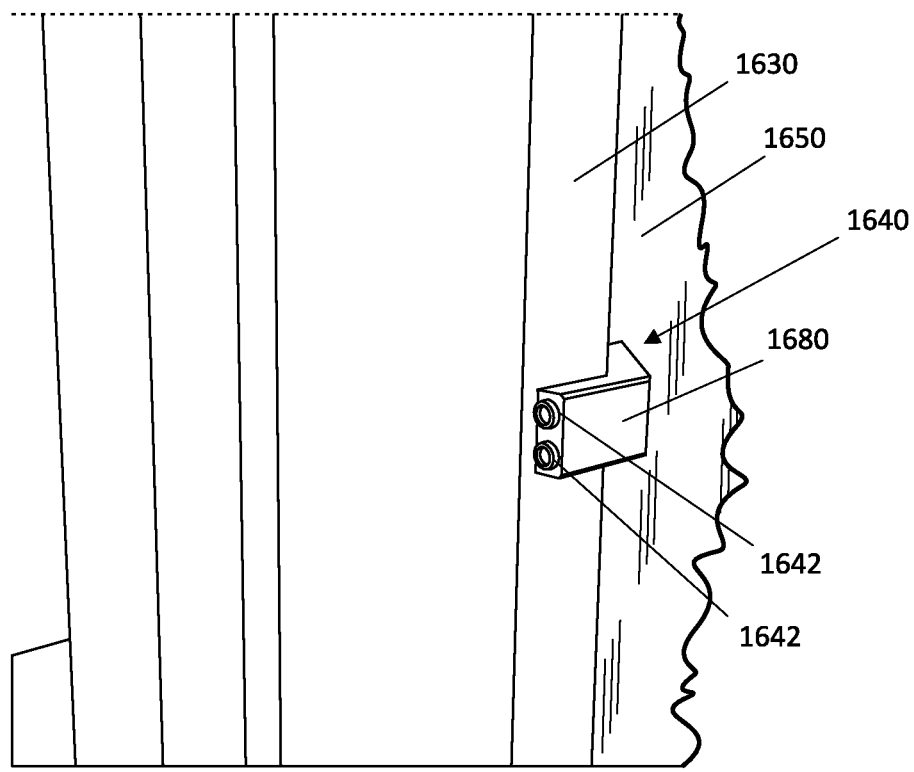
FIG. 16 illustrates an example of a detection device mounted to a doorframe.

FIG. 16 illustrates an example of a detection device 1640 mounted next to a doorframe 1630. In some examples a detection device 1640 mounts to a wall 1650 beside the doorframe 1630 and fits around the doorframe 1630 to angle one or more signal generators 1642 to be directed at an opposite side of the doorframe 1630. The detection device 1640 includes a housing 1680 that mounts beside the doorframe 1630 for housing electrical components of the detection device 1640 such as the microcontroller, communications devices, power over Ethernet bus, and the like. In other examples, the detection device 1640 is mounted inside the doorframe 1630 such that the housing 1680 is fitted inside a hole in the doorframe 1630.

In a further example, the detection device 1640 can be mounted onto the door itself, and can detect that the door is open and that an asset crossed a threshold defined by the doorframe 1630. In this example, the detection device 1640 can include a position sensor that detects whether the door is opened or closed. Alternatively, the detection device 1640 can include an accelerometer that detects whether or not the door has moved, and the detected movement can be used to determine whether the door is opened or closed. In such examples, the detection device 1640 can be battery powered. When the detection device 1640 detects that the door is closed, the detection device 1640 can be powered off to save battery life.

Figure 17:
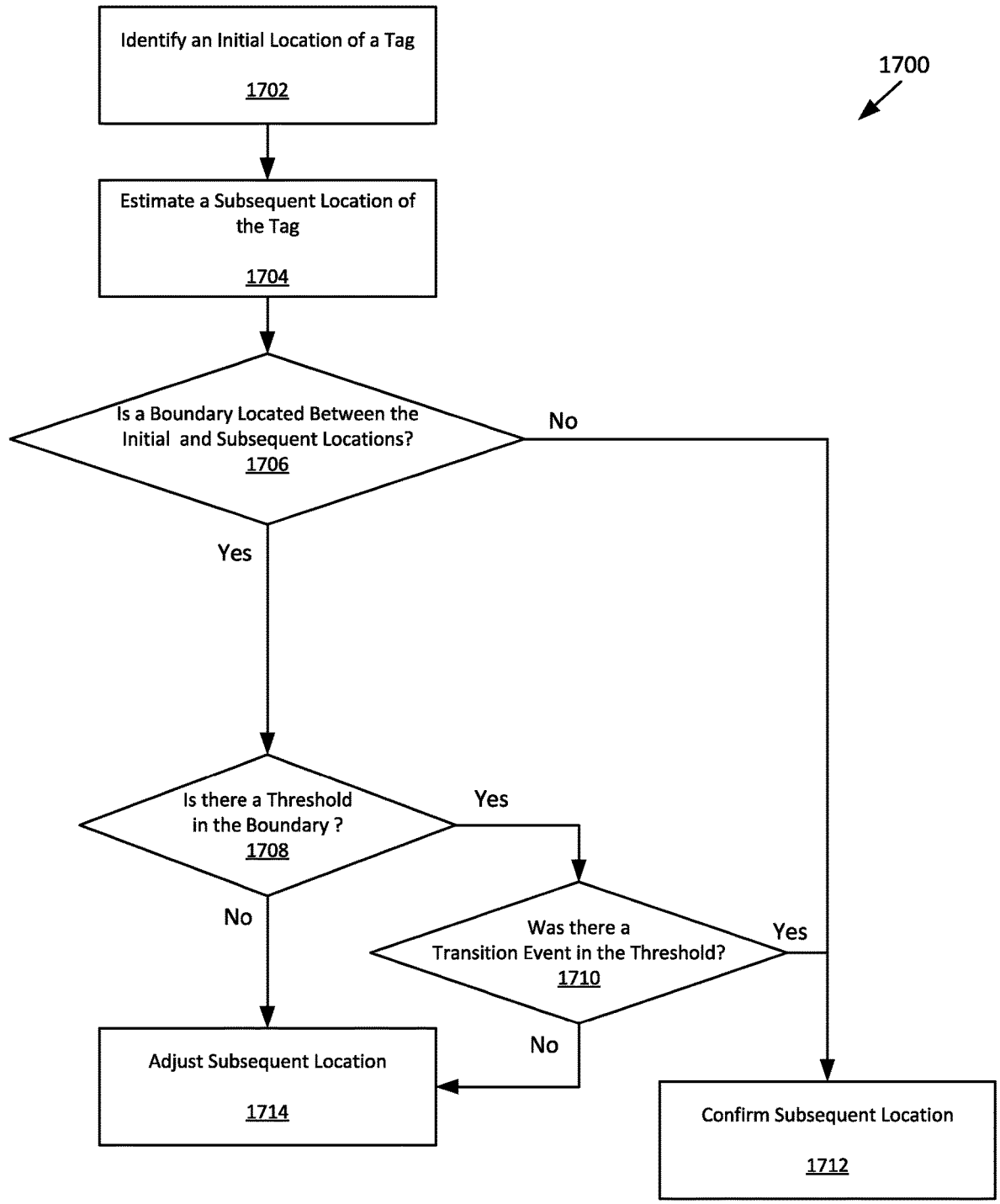
FIG. 17 illustrates an example method performed by a location system.

FIG. 17 illustrates an example method 1700 performed by the location system 1200. The method 1700 is similar to the process 400 described above with reference to FIG. 4.

At operation 1702, the location system 1200 identifies an initial location of the tag 1260. The location system 1200 may identify the initial location based on the transmission of a first signal from the tag 1260 to multiple receivers in the example environment 1201. Based on the times at which the receivers receive the first signal, as well as the locations of the receivers, the location system 1200 may identify the initial location of the tag 1260.

At operation 1704, the location system 1200 estimates a subsequent location of the tag 1260. The location system 1200 may estimate the subsequent location based on the transmission of a second signal from the tag 1260 to multiple receivers in the example environment 1201. In some cases, the tag 1260 transmits the second signal after the first signal. Based on the times at which the receivers receive the second signal, as well as the locations of the receivers, the location system 1200 estimates the subsequent location of the tag 1260.

At operation 1706, the location system 1200 determines whether a boundary is located between the initial and subsequent locations of the tag 1260. The location system 1200 can reference the environment database 1285 or a boundary map of the example environment 1201 to identify whether a boundary is present between the initial and subsequent locations of the tag 1260. For example, the location system 1200 may compare a line segment between the initial location and the subsequent location to the boundary map in order to determine whether the line segment intersects a boundary in the example environment 1201.

When the location system 1200 determines that a boundary is not located between the initial location and the subsequent location (i.e., "No" at operation 1706), the location system 1200 confirms the subsequent location of the tag 1260 at operation 1712. In some examples, the location system 1200 includes further operations to transmit a message to a reporting system that indicates the subsequent location is confirmed as the true location of the tag 1260.

When the location system 1200 determines that a boundary is located between the initial location and the subsequent location (i.e., "Yes" at operation 1706), the location system 1200 at operation 1708 determines whether the boundary has a threshold 1220. The location system 1200 can reference the environment database 1285 or a boundary map to identify whether the boundary has a threshold. In some examples, the location system 1200 determines that there is a threshold in the boundary when a threshold is at least partly within the boundary.

When the location system 1200 determines that the boundary does not have a threshold (i.e., "No" at operation 1708), the location system 1200 at operation 1714 adjusts the subsequent location of the tag 1260. In some examples, the location system 1200 adjusts the subsequent location of the tag 1260 to be on the same side of the boundary as the initial location of the tag 1260. In some examples, the location system 1200 includes further operations to transmit a message to a reporting system that indicates that the subsequent location of the tag 1260 has been adjusted to a new subsequent location.

When the location system 1200 determines that the boundary has a threshold (i.e., "Yes" at operation 1708), the location system 1200 at operation 1710 determines whether there is a transition event received from a detection device. In some examples, the detection device is identified as being positioned within the threshold. In some examples, the location system 1200 determines a path range based on an expected movement of the tag 1260 during a time interval between the first and second signal transmissions, and in response to determining that the boundary has a threshold, the location system 1200 determines whether the transition event is within the path range.

When the location system 1200 determines that a transition event was detected by a detection device (i.e., "Yes" at operation 1710), the location system 1200 confirms the subsequent location of the tag 1260 at operation 1712. In some examples, the location system 1200 includes further operations to transmit a message to a reporting system to indicate the subsequent location as the true location of the tag 1260.

When the location system 1200 determines that a transition event was not detected by a detection device (i.e., "No" at operation 1710), the location system 1200 adjusts the subsequent location of the tag 1260 at operation 1714. In some examples, the location system 1200 adjusts the subsequent location of the tag 1260 to be on the same side of the threshold 1220 as the initial location of the tag 1260 (i.e., to indicate that the tag 1260 and associated asset 1262 did not cross the threshold 1220 in the boundary).

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A method, comprising:
identifying a first location of a tag based on a first wireless signal received from the tag, the first wireless signal being transmitted by the at least one tag at a first transmission time;
estimating a second location of the tag based on a second wireless signal from the tag, the second wireless signal being transmitted by the tag at a second transmission time;
determining whether a boundary is between the first location and the second location of the tag;
determining whether the boundary includes an opening;
determining whether an asset associated with the tag in the second location passes through the opening; and
adjusting the second location of the tag to be on a same side of the boundary as the first location of the tag when the boundary is located between the first location and the second location and the asset associated with the tag in the second location is determined not to have passed through the opening of the boundary; and
transmit a message to a reporting system indicating the adjusted second location of the tag.

2. The method of claim 1, further comprising transmitting a message indicating that the second location is confirmed when the asset associated with the tag is determined to have passed through the opening of the boundary.

3. The method of claim 1, further comprising adjusting the second location of the tag to be on the same side of the boundary as the first location of the tag when the boundary does not have the opening.

4. The method of claim 1, wherein estimating the second location is done by determining a time lag in the first and second wireless signals transmitted between the tag and a receiver.

5. The method of claim 1, further comprising:
defining a path range based on an expected movement of the tag during a time interval between the first and second wireless signals; and
determining whether a transition event is within the path range.

6. The method of claim 5, wherein the transition event is detected by sensing the asset associated with the tag passing through the opening.

7. A location system, comprising:
a tag associated with an asset;

at least one receiver configured to receive wireless signals from the tag; and a device that includes at least one processor, and memory storing instructions that, when executed by the at least one processor, cause the at least one processor to:

identify a first location of the tag based on a first wireless signal from the tag that is received by the at least one receiver;

estimate a second location of the tag based on a second wireless signal from the tag that is received by the at least one receiver;

determine whether a boundary is located between the first location of the tag and the second location of the tag;

determine whether the boundary includes an opening;

determine whether the asset associated with the tag in the second location passes through the opening;

adjust the second location of the tag to be on a same side of the boundary as the first location of the tag when the boundary is located between the first location and the second location and the asset associated with the tag in the second location is determined not to have passed through the opening; and transmit a message to a reporting system indicating the adjusted second location of the tag.

8. The location system of claim 7, wherein the instructions further cause the at least one processor to transmit a message confirming the second location of the tag when the asset associated with the tag is determined to have passed through the opening of the boundary.

9. The location system of claim 7, wherein the opening includes a doorway for entering and exiting a room within a clinical environment.

10. The location system of claim 9, further comprising a detection device that transmits a signal across opposite sides of the doorway.

11. The location system of claim 7, wherein the opening includes a threshold defined between hallway segments within a clinical environment.

12. The location system of claim 11, further comprising a detection device that transmits a signal across opposite walls between the hallway segments.

13. The location system of claim 7, further comprising a detection device that detects the transition event by sensing the asset passing through the opening.

14. The location system of claim 13, wherein the detection device is a range finder that generates a signal to measure a distance in the opening, and the asset associated with the tag passing through the opening is detected when the asset decreases the measured distance in the opening.

15. The location system of claim 13, wherein the detection device includes a signal generator on one side of the opening, and a signal receiver on an opposite side of the opening, and the asset associated with the tag passing through the opening is detected when a signal transmitted across the opening between the signal generator and the signal receiver is interrupted by the asset.

16. The location system of claim 7, further comprising a location engine that estimates the second location of the at least one tag by determining a time lag in the first and second wireless signals transmitted between the at least one tag and the at least one receiver.

17. The location system of claim 7, wherein a path range is defined around the identified first location of the tag based on an expected movement of the tag during a time interval between the first wireless signal and the second wireless signal, and in response to determining that the boundary has the opening, the instructions further cause the at least one processor to determine whether a transition event is within the path range.

* * * * *